US009950135B2

(12) United States Patent
Winter

(10) Patent No.: US 9,950,135 B2
(45) Date of Patent: Apr. 24, 2018

(54) MAINTAINING AN EXHALATION VALVE SENSOR ASSEMBLY

(71) Applicant: Covidien LP, Boulder, CO (US)

(72) Inventor: David Phillip Winter, Encinitas, CA (US)

(73) Assignee: Covidien LP, Boulder, CO (US)

( * ) Notice: Subject to any disclaimer, the term of this patent is extended or adjusted under 35 U.S.C. 154(b) by 1035 days.

(21) Appl. No.: 13/839,676

(22) Filed: Mar. 15, 2013

(65) Prior Publication Data

US 2014/0276176 A1    Sep. 18, 2014

(51) Int. Cl.
*A61M 16/20* (2006.01)
*A61B 5/087* (2006.01)
*A61M 16/10* (2006.01)

(52) U.S. Cl.
CPC .......... *A61M 16/208* (2013.01); *A61B 5/087* (2013.01); *A61M 16/206* (2014.02); *A61B 2560/0443* (2013.01); *A61B 2562/0247* (2013.01); *A61M 16/1065* (2014.02); *A61M 2205/11* (2013.01); *A61M 2209/06* (2013.01)

(58) Field of Classification Search
CPC .......... A61M 2209/06; A61M 16/1065; A61M 16/206; A61M 16/208; A61M 2205/11; A61B 2560/0443; A61B 2562/0247; A61B 5/087
USPC ...................................... 206/485.1, 493, 507
See application file for complete search history.

(56) References Cited

U.S. PATENT DOCUMENTS

| 2,619,986 | A | 12/1952 | Goepfrich |
| 3,444,857 | A | 5/1969 | Godel |
| 3,481,333 | A | 12/1969 | Garrison |
| 3,485,243 | A | 12/1969 | Bird |
| 3,500,826 | A | 3/1970 | Haire |
| 3,688,794 | A | 9/1972 | Bird et al. |
| 4,066,176 | A | 1/1978 | Honeycutt |
| 4,207,884 | A | 6/1980 | Isaacson |
| 4,241,756 | A | 12/1980 | Bennett et al. |
| 4,406,291 | A | 9/1983 | Schwesinger |
| 4,491,225 | A * | 1/1985 | Baillod ............... B65D 81/075 206/507 |
| 4,527,557 | A | 7/1985 | DeVries et al. |
| 4,587,967 | A | 5/1986 | Chu et al. |
| 4,608,976 | A | 9/1986 | Suchy |
| 4,699,137 | A | 10/1987 | Schroeder |
| RE32,553 | E | 12/1987 | Bennett et al. |

(Continued)

FOREIGN PATENT DOCUMENTS

| EP | 0266963 | 5/1988 |
| EP | 0459647 | 12/1991 |

(Continued)

OTHER PUBLICATIONS

7200 Series Ventilator, Options, and Accessories: Operator's Manual. Nellcor Puritan Bennett, Part No. 22300 A, Sep. 1990.

(Continued)

*Primary Examiner* — Peter S Vasat

(57) ABSTRACT

The disclosure describes an exhalation valve sensor assembly. The disclosure describes a novel exhalation valve sensor assembly that is configured for refurbishing. Accordingly, the disclosure further describes systems and methods for maintaining an exhalation valve assembly and describes a kit for refurbishing an exhalation valve sensor assembly.

13 Claims, 10 Drawing Sheets

(56) References Cited

U.S. PATENT DOCUMENTS

| | | | |
|---|---|---|---|
| 4,712,580 A | 12/1987 | Gilman et al. | |
| 4,727,871 A | 3/1988 | Smargiassi et al. | |
| 4,747,403 A | 5/1988 | Gluck et al. | |
| 4,752,089 A | 6/1988 | Carter | |
| D300,271 S | 3/1989 | Rudolph et al. | |
| D300,272 S | 3/1989 | Rudolph et al. | |
| D300,273 S | 3/1989 | Rudolph et al. | |
| D305,165 S | 12/1989 | Rudolph et al. | |
| 4,921,642 A | 5/1990 | LaTorraca | |
| 4,954,799 A | 9/1990 | Kumar | |
| 4,957,107 A | 9/1990 | Sipin | |
| 4,991,576 A | 2/1991 | Henkin et al. | |
| 4,993,269 A | 2/1991 | Guillaume et al. | |
| 5,000,173 A | 3/1991 | Zalkin et al. | |
| 5,020,532 A | 6/1991 | Mahoney et al. | |
| 5,038,621 A | 8/1991 | Stupecky | |
| 5,057,822 A | 10/1991 | Hoffman | |
| 5,072,729 A | 12/1991 | DeVries | |
| 5,072,737 A | 12/1991 | Goulding | |
| 5,109,838 A | 5/1992 | Elam | |
| 5,127,400 A | 7/1992 | DeVries et al. | |
| 5,131,387 A | 7/1992 | French et al. | |
| 5,134,995 A | 8/1992 | Gruenke et al. | |
| 5,146,092 A | 9/1992 | Apperson et al. | |
| 5,150,291 A | 9/1992 | Cummings et al. | |
| 5,153,436 A | 10/1992 | Apperson et al. | |
| 5,161,525 A | 11/1992 | Kimm et al. | |
| 5,168,868 A | 12/1992 | Hicks | |
| 5,178,155 A | 1/1993 | Mault | |
| 5,230,727 A * | 7/1993 | Pound | A61M 16/105 |
| | | | 210/446 |
| 5,237,987 A | 8/1993 | Anderson et al. | |
| 5,255,675 A | 10/1993 | Kolobow | |
| 5,259,373 A | 11/1993 | Gruenke et al. | |
| 5,269,293 A | 12/1993 | Löser et al. | |
| 5,271,389 A | 12/1993 | Isaza et al. | |
| 5,277,175 A | 1/1994 | Riggs et al. | |
| 5,279,549 A | 1/1994 | Ranford | |
| 5,299,568 A | 4/1994 | Forare et al. | |
| 5,301,667 A | 4/1994 | McGrail et al. | |
| 5,301,921 A | 4/1994 | Kumar | |
| 5,303,699 A | 4/1994 | Bonassa et al. | |
| 5,309,901 A | 5/1994 | Beaussant | |
| 5,316,009 A | 5/1994 | Yamada et al. | |
| 5,319,540 A | 6/1994 | Isaza et al. | |
| 5,325,861 A | 7/1994 | Goulding | |
| 5,331,995 A | 7/1994 | Westfall et al. | |
| 5,333,606 A | 8/1994 | Schneider et al. | |
| 5,335,656 A | 8/1994 | Bowe et al. | |
| 5,337,739 A * | 8/1994 | Lehman | A61B 5/097 |
| | | | 128/205.27 |
| 5,339,807 A | 8/1994 | Carter | |
| 5,343,857 A | 9/1994 | Schneider et al. | |
| 5,343,858 A | 9/1994 | Winefordner et al. | |
| 5,351,522 A | 10/1994 | Lura | |
| 5,355,893 A | 10/1994 | Mick et al. | |
| 5,357,946 A | 10/1994 | Kee et al. | |
| 5,360,000 A | 11/1994 | Carter | |
| 5,368,019 A | 11/1994 | LaTorraca | |
| 5,368,021 A | 11/1994 | Beard et al. | |
| 5,369,277 A | 11/1994 | Knodle et al. | |
| 5,383,449 A | 1/1995 | Forare et al. | |
| 5,385,142 A | 1/1995 | Brady et al. | |
| 5,390,666 A | 2/1995 | Kimm et al. | |
| 5,398,677 A | 3/1995 | Smith | |
| 5,401,135 A | 3/1995 | Stoen et al. | |
| D357,532 S | 4/1995 | McCulloch | |
| 5,402,796 A | 4/1995 | Packer et al. | |
| 5,407,174 A | 4/1995 | Kumar | |
| 5,413,110 A | 5/1995 | Cummings et al. | |
| 5,438,980 A | 8/1995 | Phillips | |
| 5,443,075 A | 8/1995 | Holscher | |
| 5,452,714 A | 9/1995 | Anderson et al. | |
| 5,467,766 A | 11/1995 | Ansite et al. | |
| 5,484,270 A | 1/1996 | Adahan | |
| 5,494,028 A | 2/1996 | DeVries et al. | |
| 5,497,767 A | 3/1996 | Olsson et al. | |
| 5,503,140 A | 4/1996 | Winefordner et al. | |
| 5,513,631 A | 5/1996 | McWilliams | |
| 5,517,983 A | 5/1996 | Deighan et al. | |
| 5,520,071 A | 5/1996 | Jones | |
| 5,524,615 A | 6/1996 | Power | |
| 5,531,221 A | 7/1996 | Power | |
| 5,540,220 A | 7/1996 | Gropper et al. | |
| 5,542,415 A | 8/1996 | Brady | |
| 5,542,416 A | 8/1996 | Chalvignac | |
| 5,544,674 A | 8/1996 | Kelly | |
| 5,546,935 A | 8/1996 | Champeau | |
| 5,549,106 A | 8/1996 | Gruenke et al. | |
| 5,568,910 A | 10/1996 | Koehler et al. | |
| 5,575,283 A | 11/1996 | Sjoestrand | |
| 5,596,984 A | 1/1997 | O'Mahony et al. | |
| 5,598,838 A | 2/1997 | Servidio et al. | |
| 5,606,968 A | 3/1997 | Mang | |
| 5,616,923 A | 4/1997 | Rich et al. | |
| 5,617,847 A | 4/1997 | Howe | |
| 5,630,411 A | 5/1997 | Holscher | |
| 5,632,270 A | 5/1997 | O'Mahony et al. | |
| 5,645,048 A | 7/1997 | Brodsky et al. | |
| 5,657,750 A | 8/1997 | Colman et al. | |
| 5,660,171 A | 8/1997 | Kimm et al. | |
| 5,662,099 A | 9/1997 | Tobia et al. | |
| 5,664,560 A | 9/1997 | Merrick et al. | |
| 5,664,562 A | 9/1997 | Bourdon | |
| 5,671,767 A | 9/1997 | Kelly | |
| 5,672,041 A | 9/1997 | Ringdahl et al. | |
| 5,673,689 A | 10/1997 | Power | |
| 5,678,537 A | 10/1997 | Bathe et al. | |
| 5,683,232 A | 11/1997 | Adhan | |
| 5,692,497 A | 12/1997 | Schnitzer et al. | |
| 5,693,944 A | 12/1997 | Rich | |
| 5,694,926 A | 12/1997 | DeVries et al. | |
| 5,697,363 A | 12/1997 | Hart | |
| 5,701,883 A | 12/1997 | Hete et al. | |
| 5,701,889 A | 12/1997 | Danon | |
| 5,715,812 A | 2/1998 | Deighan et al. | |
| 5,762,480 A | 6/1998 | Adahan | |
| 5,771,884 A | 6/1998 | Yarnall et al. | |
| 5,789,660 A | 8/1998 | Kofoed et al. | |
| 5,791,339 A | 8/1998 | Winter | |
| 5,794,614 A | 8/1998 | Gruenke et al. | |
| 5,794,986 A | 8/1998 | Gansel et al. | |
| 5,797,393 A | 8/1998 | Kohl | |
| 5,803,064 A | 9/1998 | Phelps et al. | |
| 5,813,399 A | 9/1998 | Isaza et al. | |
| 5,823,179 A | 10/1998 | Grychowski et al. | |
| 5,826,575 A | 10/1998 | Lall | |
| 5,829,441 A | 11/1998 | Kidd et al. | |
| 5,845,636 A | 12/1998 | Gruenke et al. | |
| 5,857,458 A | 1/1999 | Tham et al. | |
| 5,864,938 A | 2/1999 | Gansel et al. | |
| 5,865,168 A | 2/1999 | Isaza | |
| 5,868,133 A | 2/1999 | DeVries et al. | |
| 5,875,783 A | 3/1999 | Kullik | |
| 5,876,352 A | 3/1999 | Weismann | |
| 5,881,717 A | 3/1999 | Isaza | |
| 5,881,722 A | 3/1999 | DeVries et al. | |
| 5,881,723 A | 3/1999 | Wallace et al. | |
| 5,884,623 A | 3/1999 | Winter | |
| 5,906,204 A | 5/1999 | Beran et al. | |
| 5,909,731 A | 6/1999 | O'Mahony et al. | |
| 5,915,379 A | 6/1999 | Wallace et al. | |
| 5,915,380 A | 6/1999 | Wallace et al. | |
| 5,915,382 A | 6/1999 | Power | |
| 5,918,597 A | 7/1999 | Jones et al. | |
| 5,921,238 A | 7/1999 | Bourdon | |
| 5,927,274 A | 7/1999 | Servidio et al. | |
| 5,927,275 A | 7/1999 | Loeser | |
| 5,931,160 A | 8/1999 | Gilmore et al. | |
| 5,934,274 A | 8/1999 | Merrick et al. | |
| 5,937,854 A | 8/1999 | Stenzier | |
| 5,937,856 A | 8/1999 | Jonasson et al. | |
| 5,941,846 A | 8/1999 | Duffy et al. | |
| 5,957,130 A | 9/1999 | Krahbichler et al. | |

(56) References Cited

U.S. PATENT DOCUMENTS

| | | |
|---|---|---|
| 6,024,089 A | 2/2000 | Wallace et al. |
| 6,041,777 A | 3/2000 | Faithfull et al. |
| 6,041,780 A | 3/2000 | Richard et al. |
| 6,047,860 A | 4/2000 | Sanders |
| 6,073,630 A | 6/2000 | Adahan |
| 6,076,523 A | 6/2000 | Jones et al. |
| D429,330 S | 8/2000 | Hoenig |
| 6,095,139 A | 8/2000 | Psaros |
| 6,095,140 A | 8/2000 | Poon et al. |
| 6,099,481 A | 8/2000 | Daniels et al. |
| 6,102,038 A | 8/2000 | DeVries |
| 6,106,480 A | 8/2000 | Gama De Abreu et al. |
| 6,116,240 A | 9/2000 | Merrick et al. |
| 6,116,242 A | 9/2000 | Frye et al. |
| 6,116,464 A | 9/2000 | Sanders |
| 6,119,686 A | 9/2000 | Somerson et al. |
| 6,123,073 A | 9/2000 | Schlawin et al. |
| 6,123,074 A | 9/2000 | Hete et al. |
| 6,131,571 A | 10/2000 | Lampotang et al. |
| 6,135,106 A | 10/2000 | Dirks et al. |
| 6,135,967 A | 10/2000 | Fiorenza et al. |
| 6,142,150 A | 11/2000 | O'Mahoney et al. |
| 6,148,814 A | 11/2000 | Clemmer et al. |
| 6,152,132 A | 11/2000 | Psaros |
| 6,152,135 A | 11/2000 | DeVries et al. |
| 6,155,986 A | 12/2000 | Brydon et al. |
| 6,158,432 A | 12/2000 | Biondi et al. |
| 6,161,539 A | 12/2000 | Winter |
| 6,176,234 B1 | 1/2001 | Salter et al. |
| 6,179,784 B1 | 1/2001 | Daniels et al. |
| 6,192,885 B1 | 2/2001 | Jalde |
| 6,196,222 B1 | 3/2001 | Heinonen et al. |
| 6,203,502 B1 | 3/2001 | Hilgendorf et al. |
| 6,217,524 B1 | 4/2001 | Orr et al. |
| 6,220,245 B1 | 4/2001 | Takabayashi et al. |
| 6,227,196 B1 | 5/2001 | Jaffe et al. |
| 6,269,810 B1 | 8/2001 | Brooker et al. |
| 6,269,812 B1 | 8/2001 | Wallace et al. |
| 6,273,444 B1 | 8/2001 | Power |
| 6,283,119 B1 | 9/2001 | Bourdon |
| 6,287,264 B1 | 9/2001 | Hoffman |
| 6,295,330 B1 | 9/2001 | Skog et al. |
| 6,295,985 B1 | 10/2001 | Kock et al. |
| 6,305,372 B1 | 10/2001 | Servidio |
| 6,305,373 B1 | 10/2001 | Wallace et al. |
| 6,306,098 B1 | 10/2001 | Orr et al. |
| 6,308,706 B1 | 10/2001 | Lammers et al. |
| 6,309,360 B1 | 10/2001 | Mault |
| 6,312,389 B1 | 11/2001 | Kofoed et al. |
| 6,321,748 B1 | 11/2001 | O'Mahoney |
| 6,325,785 B1 | 12/2001 | Babkes et al. |
| 6,325,978 B1 | 12/2001 | Labuda et al. |
| 6,349,922 B1 | 2/2002 | Rydin |
| 6,357,438 B1 | 3/2002 | Hansen |
| 6,358,215 B1 | 3/2002 | Ricciardelli |
| 6,360,745 B1 | 3/2002 | Wallace et al. |
| 6,369,838 B1 | 4/2002 | Wallace et al. |
| 6,371,113 B1 | 4/2002 | Tobia et al. |
| 6,390,091 B1 | 5/2002 | Banner et al. |
| 6,394,962 B1 | 5/2002 | Gama De Abreu et al. |
| 6,402,697 B1 | 6/2002 | Calkins et al. |
| 6,408,848 B1 | 6/2002 | Feldman et al. |
| 6,412,483 B1 | 7/2002 | Jones et al. |
| 6,415,788 B1 | 7/2002 | Clawson et al. |
| 6,419,634 B1 | 7/2002 | Gaston, IV et al. |
| 6,439,229 B1 | 8/2002 | Du et al. |
| 6,457,472 B1 | 10/2002 | Schwartz et al. |
| 6,463,930 B2 | 10/2002 | Biondi et al. |
| 6,467,478 B1 | 10/2002 | Merrick et al. |
| 6,471,658 B1 | 10/2002 | Daniels et al. |
| 6,484,719 B1 | 11/2002 | Berthon-Jones |
| 6,523,537 B1 | 2/2003 | Mas Marfany |
| 6,523,538 B1 | 2/2003 | Wikefeldt |
| 6,526,970 B2 | 3/2003 | DeVries et al. |
| 6,532,957 B2 | 3/2003 | Berthon-Jones |
| 6,532,960 B1 | 3/2003 | Yurko |
| 6,540,689 B1 | 4/2003 | Orr et al. |
| 6,543,449 B1 | 4/2003 | Woodring et al. |
| 6,546,930 B1 | 4/2003 | Emerson et al. |
| 6,550,479 B1 | 4/2003 | Duxbury |
| 6,553,991 B1 | 4/2003 | Isaza |
| 6,553,992 B1 | 4/2003 | Berthon-Jones et al. |
| 6,557,553 B1 | 5/2003 | Borrello |
| 6,557,554 B1 | 5/2003 | Sugiura |
| 6,564,798 B1 | 5/2003 | Jalde |
| 6,571,795 B2 | 6/2003 | Bourdon |
| 6,572,561 B2 | 6/2003 | Mault |
| 6,575,163 B1 | 6/2003 | Berthon-Jones |
| 6,575,164 B1 | 6/2003 | Jaffe et al. |
| 6,575,165 B1 | 6/2003 | Cook et al. |
| 6,575,918 B2 | 6/2003 | Kline |
| 6,584,973 B1 | 7/2003 | Biondi et al. |
| 6,606,994 B1 | 8/2003 | Clark |
| 6,616,615 B2 | 9/2003 | Mault |
| 6,616,896 B2 | 9/2003 | Labuda et al. |
| 6,619,289 B1 | 9/2003 | Mashak |
| 6,622,725 B1 | 9/2003 | Fisher et al. |
| 6,622,726 B1 | 9/2003 | Du |
| 6,629,934 B2 | 10/2003 | Mault et al. |
| 6,631,716 B1 | 10/2003 | Robinson et al. |
| 6,644,310 B1 | 11/2003 | Delache et al. |
| 6,648,831 B2 | 11/2003 | Orr et al. |
| 6,648,832 B2 | 11/2003 | Orr et al. |
| 6,659,962 B2 | 12/2003 | Ricciardelli |
| 6,668,824 B1 | 12/2003 | Isaza et al. |
| 6,668,828 B1 | 12/2003 | Figley et al. |
| 6,668,829 B2 | 12/2003 | Biondi et al. |
| 6,675,801 B2 | 1/2004 | Wallace et al. |
| 6,688,307 B2 | 2/2004 | Berthon-Jones |
| 6,691,702 B2 | 2/2004 | Appel et al. |
| 6,718,974 B1 | 4/2004 | Moberg |
| 6,725,447 B1 | 4/2004 | Gilman et al. |
| 6,729,331 B2 | 5/2004 | Kay |
| 6,739,334 B2 | 5/2004 | Valeij |
| 6,739,337 B2 | 5/2004 | Isaza |
| 6,755,193 B2 | 6/2004 | Berthon-Jones et al. |
| 6,761,167 B1 | 7/2004 | Nadjafizadeh et al. |
| 6,761,168 B1 | 7/2004 | Nadjafizadeh et al. |
| 6,763,829 B2 | 7/2004 | Jaffe et al. |
| 6,722,359 B2 | 8/2004 | Chalvignac |
| 6,723,055 B2 | 8/2004 | Hoffman |
| 6,772,762 B2 | 8/2004 | Piesinger |
| 6,805,121 B1 | 10/2004 | Flood et al. |
| 6,810,876 B2 | 11/2004 | Berthon-Jones |
| 6,814,074 B1 | 11/2004 | Nadjafizadeh et al. |
| 6,815,211 B1 | 11/2004 | Blazewicz et al. |
| 6,840,906 B2 | 1/2005 | Gama De Abreu et al. |
| 6,866,040 B1 | 3/2005 | Bourdon |
| 6,877,511 B2 | 4/2005 | DeVries et al. |
| 6,886,558 B2 | 5/2005 | Tanaka et al. |
| 6,896,713 B1 | 5/2005 | Eckerbom et al. |
| 6,908,438 B2 | 6/2005 | Orr et al. |
| 6,938,619 B1 | 9/2005 | Hickle |
| 6,954,702 B2 | 10/2005 | Pierry et al. |
| 6,955,651 B2 | 10/2005 | Kück et al. |
| 6,960,854 B2 | 11/2005 | Nadjafizadeh et al. |
| 6,968,840 B2 | 11/2005 | Smith et al. |
| 6,986,351 B2 | 1/2006 | Figley et al. |
| 6,990,980 B2 | 1/2006 | Richey et al. |
| 7,004,168 B2 | 2/2006 | Mace et al. |
| D518,172 S | 3/2006 | Britten et al. |
| 7,017,574 B2 | 3/2006 | Biondi et al. |
| 7,018,340 B2 | 3/2006 | Jaffe et al. |
| 7,032,589 B2 | 4/2006 | Kerchanin, II et al. |
| 7,036,504 B2 | 5/2006 | Wallace et al. |
| 7,040,315 B1 | 5/2006 | Stromberg |
| 7,040,316 B2 | 5/2006 | Connelly et al. |
| 7,040,321 B2 | 5/2006 | Göbel |
| 7,043,979 B2 | 5/2006 | Smith et al. |
| 7,066,175 B2 | 6/2006 | Hamilton et al. |
| 7,066,176 B2 | 6/2006 | Jaffe et al. |
| 7,066,177 B2 | 6/2006 | Pittaway et al. |
| 7,074,196 B2 | 7/2006 | Kück et al. |
| 7,077,131 B2 | 7/2006 | Hansen |

(56) References Cited

U.S. PATENT DOCUMENTS

| | | |
|---|---|---|
| RE39,225 E | 8/2006 | Isaza et al. |
| 7,117,438 B2 | 10/2006 | Wallace et al. |
| 7,118,537 B2 | 10/2006 | Baddour |
| 7,121,277 B2 | 10/2006 | Ström |
| 7,128,069 B2 | 10/2006 | Farrugia et al. |
| 7,135,001 B2 | 11/2006 | Orr et al. |
| 7,137,389 B2 | 11/2006 | Berthon-Jones |
| 7,152,604 B2 | 12/2006 | Hickle et al. |
| 7,168,597 B1 | 1/2007 | Jones et al. |
| D536,443 S | 2/2007 | Latsos |
| 7,183,552 B2 | 2/2007 | Russell |
| 7,195,013 B2 | 3/2007 | Lurie |
| 7,210,478 B2 | 5/2007 | Banner et al. |
| 7,222,623 B2 | 5/2007 | DeVries et al. |
| 7,241,269 B2 | 7/2007 | McCawley et al. |
| 7,270,126 B2 | 9/2007 | Wallace et al. |
| 7,275,540 B2 | 10/2007 | Bolam |
| 7,291,115 B2 | 11/2007 | Cardona Burrul |
| 7,291,851 B2 | 11/2007 | DelFavero et al. |
| 7,302,949 B2 | 12/2007 | Pelerossi et al. |
| 7,320,321 B2 | 1/2008 | Pranger et al. |
| 7,334,578 B2 | 2/2008 | Biondi et al. |
| 7,335,164 B2 | 2/2008 | Mace et al. |
| 7,341,563 B2 | 3/2008 | Rich et al. |
| 7,347,205 B2 | 3/2008 | Levi |
| 7,347,825 B2 | 3/2008 | Vaughan et al. |
| 7,363,085 B1 | 4/2008 | Benser et al. |
| 7,367,337 B2 | 5/2008 | Berton-Jones et al. |
| 7,369,757 B2 | 5/2008 | Farbarik |
| 7,370,650 B2 | 5/2008 | Nadjafizadeh et al. |
| 7,392,806 B2 | 7/2008 | Yuen et al. |
| 7,421,296 B1 | 9/2008 | Benser et al. |
| 7,427,269 B2 | 9/2008 | George et al. |
| 7,428,902 B2 | 9/2008 | Du et al. |
| 7,432,508 B2 | 10/2008 | Daniels et al. |
| 7,460,959 B2 | 12/2008 | Jafari |
| 7,475,685 B2 | 1/2009 | Dietz et al. |
| 7,484,508 B2 | 2/2009 | Younes |
| 7,487,773 B2 | 2/2009 | Li |
| 7,487,778 B2 | 2/2009 | Freitag |
| 7,500,483 B2 | 3/2009 | Colman et al. |
| 7,503,957 B2 | 3/2009 | Duquette et al. |
| 7,509,957 B2 | 3/2009 | Duquette et al. |
| 7,519,425 B2 | 4/2009 | Benser et al. |
| 7,525,663 B2 | 4/2009 | Kwok et al. |
| 7,533,670 B1 | 5/2009 | Freitag et al. |
| 7,547,285 B2 | 6/2009 | Kline |
| 7,556,038 B2 | 7/2009 | Kirby et al. |
| 7,556,042 B2 | 7/2009 | West et al. |
| 7,562,657 B2 | 7/2009 | Blanch et al. |
| 7,588,033 B2 | 9/2009 | Wondka |
| 7,610,914 B2 | 11/2009 | Bolam et al. |
| 7,617,824 B2 | 11/2009 | Doyle |
| 7,621,271 B2 | 11/2009 | Brugnoli |
| 7,634,998 B1 | 12/2009 | Fenley |
| 7,644,713 B2 | 1/2010 | Berthon-Jones |
| 7,654,802 B2 | 2/2010 | Crawford, Jr. et al. |
| 7,668,579 B2 | 2/2010 | Lynn |
| 7,686,019 B2 | 3/2010 | Weiss et al. |
| 7,694,677 B2 | 4/2010 | Tang |
| 7,699,788 B2 | 4/2010 | Kuck et al. |
| 7,717,113 B2 | 5/2010 | Andrieux |
| 7,721,735 B2 | 5/2010 | Hamilton et al. |
| 7,721,736 B2 | 5/2010 | Urias et al. |
| D618,356 S | 6/2010 | Ross |
| 7,740,591 B1 | 6/2010 | Starr et al. |
| 7,753,052 B2 | 7/2010 | Tanaka |
| 7,779,840 B2 | 8/2010 | Acker et al. |
| 7,784,461 B2 | 8/2010 | Figueiredo et al. |
| 7,810,497 B2 | 10/2010 | Pittman et al. |
| 7,814,908 B2 | 10/2010 | Psaros |
| 7,819,815 B2 | 10/2010 | Younes |
| 7,823,588 B2 | 11/2010 | Hansen |
| 7,828,741 B2 | 11/2010 | Kline et al. |
| 7,846,739 B2 | 12/2010 | von Bahr et al. |
| 7,849,854 B2 | 12/2010 | DeVries et al. |
| 7,855,716 B2 | 12/2010 | McCreary et al. |
| 7,861,716 B2 | 1/2011 | Borrello |
| 7,870,857 B2 | 1/2011 | Dhuper et al. |
| D632,796 S | 2/2011 | Ross et al. |
| D632,797 S | 2/2011 | Ross et al. |
| 7,883,471 B2 | 2/2011 | Aljuri et al. |
| 7,885,771 B2 | 2/2011 | Roecker et al. |
| 7,891,354 B2 | 2/2011 | Farbarik |
| 7,893,560 B2 | 2/2011 | Carter |
| 7,900,626 B2 | 3/2011 | Daly |
| 7,913,690 B2 | 3/2011 | Fisher et al. |
| D638,852 S | 5/2011 | Skidmore et al. |
| 7,984,714 B2 | 7/2011 | Hausmann et al. |
| D643,535 S | 8/2011 | Ross et al. |
| 7,992,557 B2 | 8/2011 | Nadjafizadeh et al. |
| 8,001,967 B2 | 8/2011 | Wallace et al. |
| D645,158 S | 9/2011 | Sanchez et al. |
| 8,021,310 B2 | 9/2011 | Sanborn et al. |
| D649,157 S | 11/2011 | Skidmore et al. |
| D652,521 S | 1/2012 | Ross et al. |
| D652,936 S | 1/2012 | Ross et al. |
| D653,749 S | 2/2012 | Winter et al. |
| 8,113,062 B2 | 2/2012 | Graboi et al. |
| D655,405 S | 3/2012 | Winter et al. |
| D655,809 S | 3/2012 | Winter et al. |
| D656,237 S | 3/2012 | Sanchez et al. |
| 8,181,648 B2 | 5/2012 | Perine et al. |
| 8,210,173 B2 | 7/2012 | Vandine |
| 8,210,174 B2 | 7/2012 | Farbarik |
| 8,240,684 B2 | 8/2012 | Ross et al. |
| 8,267,085 B2 | 9/2012 | Jafari et al. |
| 8,272,379 B2 | 9/2012 | Jafari et al. |
| 8,272,380 B2 | 9/2012 | Jafari et al. |
| 8,302,600 B2 | 11/2012 | Andrieux et al. |
| 8,302,602 B2 | 11/2012 | Andrieux et al. |
| 8,457,706 B2 | 6/2013 | Baker, Jr. |
| D692,556 S | 10/2013 | Winter |
| D693,001 S | 11/2013 | Winter |
| D701,601 S | 3/2014 | Winter |
| 8,792,949 B2 | 7/2014 | Baker, Jr. |
| D731,048 S | 6/2015 | Winter |
| D731,049 S | 6/2015 | Winter |
| D731,065 S | 6/2015 | Winter |
| D736,905 S | 8/2015 | Winter |
| D744,095 S | 11/2015 | Winter |
| 2001/0029339 A1 | 10/2001 | Orr et al. |
| 2001/0031928 A1 | 10/2001 | Orr et al. |
| 2002/0026941 A1 | 3/2002 | Bondi et al. |
| 2002/0082512 A1 | 6/2002 | Strom |
| 2002/0128566 A1 | 9/2002 | Gama De Abreu et al. |
| 2002/0138213 A1 | 9/2002 | Mault |
| 2002/0148468 A1 | 10/2002 | Valeij |
| 2003/0047188 A1 | 3/2003 | Mace et al. |
| 2003/0062045 A1 | 4/2003 | Woodring et al. |
| 2003/0111078 A1 | 6/2003 | Habashi et al. |
| 2003/0140921 A1 | 7/2003 | Smith et al. |
| 2003/0191405 A1 | 10/2003 | Rich et al. |
| 2004/0003814 A1 | 1/2004 | Banner et al. |
| 2004/0050387 A1 | 3/2004 | Younes |
| 2004/0087867 A1 | 5/2004 | Gama De Abreu et al. |
| 2004/0138577 A1 | 7/2004 | Kline |
| 2004/0186391 A1 | 9/2004 | Pierry et al. |
| 2004/0256560 A1 | 12/2004 | Russell |
| 2004/0261793 A1 | 12/2004 | Stromberg et al. |
| 2005/0005936 A1 | 1/2005 | Wondka |
| 2005/0008936 A1 | 1/2005 | Wondka |
| 2005/0034726 A1 | 2/2005 | Pittaway et al. |
| 2005/0039748 A1 | 2/2005 | Andrieux |
| 2005/0098177 A1 | 5/2005 | Haj-Yahya et al. |
| 2005/0112325 A1 | 5/2005 | Hickle |
| 2005/0124907 A1 | 6/2005 | Kuck et al. |
| 2005/0139211 A1 | 6/2005 | Alston et al. |
| 2005/0139212 A1 | 6/2005 | Bourdon |
| 2005/0150494 A1 | 7/2005 | DeVries et al. |
| 2005/0217671 A1 | 10/2005 | Fisher et al. |
| 2005/0279358 A1 | 12/2005 | Richey et al. |
| 2005/0284476 A1 | 12/2005 | Blache et al. |
| 2005/0285055 A1 | 12/2005 | DelFavero et al. |

(56) References Cited

U.S. PATENT DOCUMENTS

| | | |
|---|---|---|
| 2006/0009707 A1 | 1/2006 | Daniels et al. |
| 2006/0032499 A1 | 2/2006 | Halsnes |
| 2006/0052950 A1 | 3/2006 | Pierry et al. |
| 2006/0086357 A1 | 4/2006 | Soliman et al. |
| 2006/0129054 A1 | 6/2006 | Orr et al. |
| 2006/0130839 A1 | 6/2006 | Bassovich |
| 2006/0145078 A1 | 7/2006 | Russell |
| 2006/0201507 A1 | 9/2006 | Breen |
| 2006/0241508 A1 | 10/2006 | Jaffe et al. |
| 2006/0243278 A1 | 11/2006 | Hamilton et al. |
| 2006/0249148 A1 | 11/2006 | Younes |
| 2006/0249153 A1 | 11/2006 | DeVries et al. |
| 2006/0253038 A1 | 11/2006 | Kuck et al. |
| 2006/0278223 A1 | 12/2006 | Younes |
| 2007/0000494 A1 | 1/2007 | Banner et al. |
| 2007/0017515 A1 | 1/2007 | Wallace et al. |
| 2007/0028921 A1 | 2/2007 | Banner et al. |
| 2007/0062531 A1 | 2/2007 | Fisher et al. |
| 2007/0044798 A1 | 3/2007 | Levi |
| 2007/0068518 A1 | 3/2007 | Urias et al. |
| 2007/0068530 A1 | 3/2007 | Pacey |
| 2007/0073183 A1 | 3/2007 | Kline |
| 2007/0077200 A1 | 4/2007 | Baker |
| 2007/0095347 A1 | 5/2007 | Lampotang et al. |
| 2007/0107728 A1 | 5/2007 | Ricciardelli et al. |
| 2007/0113854 A1 | 5/2007 | Mcauliffe |
| 2007/0125377 A1 | 6/2007 | Heinonen et al. |
| 2007/0142716 A1 | 6/2007 | Biondi |
| 2007/0144521 A1 | 6/2007 | DeVries et al. |
| 2007/0144523 A1 | 6/2007 | Bolam et al. |
| 2007/0149891 A1 | 6/2007 | George et al. |
| 2007/0157930 A1 | 7/2007 | Soliman et al. |
| 2007/0157931 A1 | 7/2007 | Parker et al. |
| 2007/0163579 A1 | 7/2007 | Li et al. |
| 2007/0193579 A1 | 8/2007 | Duquette et al. |
| 2007/0199566 A1 | 8/2007 | Be'eri |
| 2007/0215154 A1 | 9/2007 | Borrello |
| 2007/0221221 A1 | 9/2007 | Cooke et al. |
| 2007/0225612 A1 | 9/2007 | Mace |
| 2007/0227537 A1 | 10/2007 | Bemister et al. |
| 2007/0232952 A1 | 10/2007 | Baddour |
| 2007/0240718 A1 | 10/2007 | Daly |
| 2007/0255160 A1 | 11/2007 | Daly |
| 2007/0272241 A1 | 11/2007 | Sanborn et al. |
| 2007/0272242 A1 | 11/2007 | Sanborn et al. |
| 2007/0273887 A1 | 11/2007 | Russell |
| 2007/0282214 A1 | 12/2007 | George et al. |
| 2007/0284361 A1 | 12/2007 | Nadjafizadeh et al. |
| 2008/0000471 A1 | 1/2008 | Bolam et al. |
| 2008/0009761 A1 | 1/2008 | Acker et al. |
| 2008/0011300 A1 | 1/2008 | Andreiux |
| 2008/0021339 A1 | 1/2008 | Gabriel et al. |
| 2008/0045825 A1 | 2/2008 | Melker et al. |
| 2008/0053438 A1 | 3/2008 | DeVries et al. |
| 2008/0053441 A1 | 3/2008 | Gottlib et al. |
| 2008/0058667 A1 | 3/2008 | Pierry et al. |
| 2008/0060646 A1 | 3/2008 | Isaza |
| 2008/0060656 A1 | 3/2008 | Isaza |
| 2008/0072896 A1 | 3/2008 | Setzer et al. |
| 2008/0072902 A1 | 3/2008 | Setzer et al. |
| 2008/0078390 A1 | 4/2008 | Milne et al. |
| 2008/0083644 A1 | 4/2008 | Janbakhsh et al. |
| 2008/0091117 A1 | 4/2008 | Choncholas et al. |
| 2008/0092894 A1 | 4/2008 | Nicolazzi et al. |
| 2008/0097234 A1 | 4/2008 | Nicolazzi et al. |
| 2008/0119753 A1 | 5/2008 | Ricciardelli et al. |
| 2008/0119754 A1 | 5/2008 | Hietala |
| 2008/0135044 A1 | 6/2008 | Freitag et al. |
| 2008/0168990 A1 | 7/2008 | Cooke et al. |
| 2008/0183094 A1 | 7/2008 | Schonfuss et al. |
| 2008/0196720 A1 | 8/2008 | Kollmeyer et al. |
| 2008/0202517 A1 | 8/2008 | Mitton et al. |
| 2008/0202518 A1 | 8/2008 | Mitton et al. |
| 2008/0214947 A1 | 9/2008 | Hunt et al. |
| 2008/0230062 A1 | 9/2008 | Tham |
| 2008/0257349 A1 | 10/2008 | Hedner et al. |
| 2008/0276939 A1 | 11/2008 | Tiedje |
| 2009/0000621 A1 | 1/2009 | Haggblom et al. |
| 2009/0007914 A1 | 1/2009 | Bateman |
| 2009/0050153 A1 | 2/2009 | Brunner |
| 2009/0056708 A1 | 3/2009 | Stenzler et al. |
| 2009/0056719 A1 | 3/2009 | Newman |
| 2009/0071478 A1 | 3/2009 | Kalfon |
| 2009/0071479 A1 | 3/2009 | Nguyen et al. |
| 2009/0078251 A1 | 3/2009 | Zucchi et al. |
| 2009/0084381 A1 | 4/2009 | DeVries et al. |
| 2009/0090359 A1 | 4/2009 | Daviet et al. |
| 2009/0107500 A1 | 4/2009 | Edwards |
| 2009/0114223 A1 | 5/2009 | Bonassa |
| 2009/0133695 A1 | 5/2009 | Rao et al. |
| 2009/0137919 A1 | 5/2009 | Bar-Lavie et al. |
| 2009/0165795 A1 | 7/2009 | Nadjafizadeh et al. |
| 2009/0171176 A1 | 7/2009 | Andersohn |
| 2009/0188502 A1 | 7/2009 | Tiedje |
| 2009/0205661 A1 | 8/2009 | Stephenson et al. |
| 2009/0205663 A1 | 8/2009 | Vandine et al. |
| 2009/0217923 A1 | 9/2009 | Boehm et al. |
| 2009/0221926 A1 | 9/2009 | Younes |
| 2009/0229612 A1 | 9/2009 | Levi et al. |
| 2009/0235935 A1 | 9/2009 | Pacey |
| 2009/0241948 A1 | 10/2009 | Clancy et al. |
| 2009/0241951 A1 | 10/2009 | Jafari et al. |
| 2009/0241952 A1 | 10/2009 | Nicolazzi et al. |
| 2009/0241953 A1 | 10/2009 | Vandine et al. |
| 2009/0241955 A1 | 10/2009 | Jafari et al. |
| 2009/0241956 A1 | 10/2009 | Baker, Jr. et al. |
| 2009/0241957 A1 | 10/2009 | Baker, Jr. |
| 2009/0241958 A1 | 10/2009 | Baker, Jr. |
| 2009/0241962 A1 | 10/2009 | Jafari et al. |
| 2009/0241964 A1 | 10/2009 | Aljuri et al. |
| 2009/0247849 A1 | 10/2009 | McCutcheon et al. |
| 2009/0247853 A1 | 10/2009 | Debreczeny |
| 2009/0247891 A1 | 10/2009 | Wood |
| 2009/0250054 A1 | 10/2009 | Loncar et al. |
| 2009/0250059 A1 | 10/2009 | Allum et al. |
| 2009/0255533 A1 | 10/2009 | Freitag et al. |
| 2009/0260625 A1 | 10/2009 | Wondka |
| 2009/0263279 A1 | 10/2009 | Kline et al. |
| 2009/0270752 A1 | 10/2009 | Coifman |
| 2009/0277448 A1 | 11/2009 | Ahlemn et al. |
| 2009/0293873 A1 | 12/2009 | Djupesland et al. |
| 2009/0293877 A1 | 12/2009 | Blanch et al. |
| 2009/0299430 A1 | 12/2009 | Daviet et al. |
| 2009/0301486 A1 | 12/2009 | Masic |
| 2009/0301487 A1 | 12/2009 | Masic |
| 2009/0301490 A1 | 12/2009 | Masic |
| 2009/0301491 A1 | 12/2009 | Masic et al. |
| 2010/0011307 A1 | 1/2010 | Desfossez et al. |
| 2010/0012126 A1 | 1/2010 | Gandini |
| 2010/0024820 A1 | 2/2010 | Bourdon |
| 2010/0031961 A1 | 2/2010 | Schmidt |
| 2010/0051026 A1 | 3/2010 | Graboi |
| 2010/0051029 A1 | 3/2010 | Jafari et al. |
| 2010/0059058 A1 | 3/2010 | Kuo |
| 2010/0069761 A1 | 3/2010 | Karst et al. |
| 2010/0071689 A1 | 3/2010 | Thiessen |
| 2010/0071692 A1 | 3/2010 | Porges |
| 2010/0071695 A1 | 3/2010 | Thiessen |
| 2010/0071696 A1 | 3/2010 | Jafari |
| 2010/0071697 A1 | 3/2010 | Jafari et al. |
| 2010/0078017 A1 | 4/2010 | Andrieux et al. |
| 2010/0078026 A1 | 4/2010 | Andrieux et al. |
| 2010/0081119 A1 | 4/2010 | Jafari et al. |
| 2010/0081955 A1 | 4/2010 | Wood, Jr. et al. |
| 2010/0099999 A1 | 4/2010 | Hemnes et al. |
| 2010/0101577 A1 | 4/2010 | Kaestle et al. |
| 2010/0106037 A1 | 4/2010 | Kacmarek et al. |
| 2010/0125227 A1 | 5/2010 | Bird |
| 2010/0137733 A1 | 6/2010 | Wang et al. |
| 2010/0139660 A1 | 6/2010 | Adahan |
| 2010/0147302 A1 | 6/2010 | Selvarajan et al. |
| 2010/0147303 A1 | 6/2010 | Jafari et al. |
| 2010/0170512 A1 | 7/2010 | Kuypers et al. |
| 2010/0175695 A1 | 7/2010 | Jamison |

(56) References Cited

U.S. PATENT DOCUMENTS

| | | |
|---|---|---|
| 2010/0179392 A1 | 7/2010 | Chang et al. |
| 2010/0180897 A1 | 7/2010 | Malgouyres |
| 2010/0185112 A1 | 7/2010 | Van Kesteren et al. |
| 2010/0186744 A1 | 7/2010 | Andrieux |
| 2010/0198095 A1 | 8/2010 | Isler |
| 2010/0218765 A1 | 9/2010 | Jafari et al. |
| 2010/0218766 A1 | 9/2010 | Milne |
| 2010/0218767 A1 | 9/2010 | Jafari et al. |
| 2010/0222692 A1 | 9/2010 | McCawley et al. |
| 2010/0236553 A1 | 9/2010 | Jafari et al. |
| 2010/0236555 A1 | 9/2010 | Jafari et al. |
| 2010/0241019 A1 | 9/2010 | Varga et al. |
| 2010/0242961 A1 | 9/2010 | Mougel et al. |
| 2010/0249549 A1 | 9/2010 | Baker, Jr. et al. |
| 2010/0249584 A1 | 9/2010 | Albertelli |
| 2010/0252042 A1 | 10/2010 | Kapust et al. |
| 2010/0268106 A1 | 10/2010 | Johnson et al. |
| 2010/0268131 A1 | 10/2010 | Efthimion |
| 2010/0269834 A1 | 10/2010 | Freitag et al. |
| 2010/0282258 A1 | 11/2010 | Tailor et al. |
| 2010/0282259 A1 | 11/2010 | Figueiredo et al. |
| 2010/0286544 A1 | 11/2010 | Tanaka et al. |
| 2010/0288283 A1 | 11/2010 | Campbell et al. |
| 2010/0292601 A1 | 11/2010 | Dompeling et al. |
| 2010/0300446 A1 | 12/2010 | Nicolazzi et al. |
| 2010/0324437 A1 | 12/2010 | Freeman et al. |
| 2010/0324439 A1 | 12/2010 | Davenport |
| 2011/0004108 A1 | 1/2011 | Peyton |
| 2011/0009762 A1 | 1/2011 | Eichler et al. |
| 2011/0011400 A1 | 1/2011 | Gentner et al. |
| 2011/0023878 A1 | 2/2011 | Thiessen |
| 2011/0023879 A1 | 2/2011 | Vandine et al. |
| 2011/0023880 A1 | 2/2011 | Thiessen |
| 2011/0023881 A1 | 2/2011 | Thiessen |
| 2011/0029910 A1 | 2/2011 | Thiessen |
| 2011/0041849 A1 | 2/2011 | Chen et al. |
| 2011/0041850 A1 | 2/2011 | Vandie et al. |
| 2011/0066060 A1 | 3/2011 | von Bahr et al. |
| 2011/0126829 A1 | 6/2011 | Carter et al. |
| 2011/0126832 A1 | 6/2011 | Winter et al. |
| 2011/0126834 A1 | 6/2011 | Winter et al. |
| 2011/0126835 A1 | 6/2011 | Winter et al. |
| 2011/0126836 A1 | 6/2011 | Winter et al. |
| 2011/0126837 A1* | 6/2011 | Winter .................. A61M 16/20 128/205.12 |
| 2011/0128008 A1 | 6/2011 | Carter |
| 2011/0132361 A1 | 6/2011 | Sanchez |
| 2011/0132362 A1 | 6/2011 | Sanchez |
| 2011/0132364 A1 | 6/2011 | Ogilvie et al. |
| 2011/0132365 A1 | 6/2011 | Patel et al. |
| 2011/0132366 A1 | 6/2011 | Ogilvie et al. |
| 2011/0132367 A1 | 6/2011 | Patel |
| 2011/0132368 A1 | 6/2011 | Sanchez et al. |
| 2011/0132369 A1 | 6/2011 | Sanchez |
| 2011/0132371 A1 | 6/2011 | Sanchez et al. |
| 2011/0133936 A1 | 6/2011 | Sanchez et al. |
| 2011/0138308 A1 | 6/2011 | Palmer et al. |
| 2011/0138309 A1 | 6/2011 | Skidmore et al. |
| 2011/0138311 A1 | 6/2011 | Palmer |
| 2011/0138315 A1 | 6/2011 | Vandine et al. |
| 2011/0138323 A1 | 6/2011 | Skidmore et al. |
| 2011/0146681 A1 | 6/2011 | Jafari et al. |
| 2011/0146683 A1 | 6/2011 | Jafari et al. |
| 2011/0154241 A1 | 6/2011 | Skidmore et al. |
| 2011/0175728 A1 | 7/2011 | Baker, Jr. |
| 2011/0196251 A1 | 8/2011 | Jourdain et al. |
| 2011/0209702 A1 | 9/2011 | Vuong et al. |
| 2011/0209704 A1 | 9/2011 | Jafari et al. |
| 2011/0209707 A1 | 9/2011 | Terhark |
| 2011/0213215 A1 | 9/2011 | Doyle et al. |
| 2011/0230780 A1 | 9/2011 | Sanborn et al. |
| 2011/0249006 A1 | 10/2011 | Wallace et al. |
| 2011/0259330 A1 | 10/2011 | Jafari et al. |
| 2011/0259332 A1 | 10/2011 | Sanchez et al. |
| 2011/0259333 A1 | 10/2011 | Sanchez et al. |
| 2011/0265024 A1 | 10/2011 | Leone et al. |
| 2011/0271960 A1 | 11/2011 | Milne et al. |
| 2011/0273299 A1 | 11/2011 | Milne et al. |
| 2012/0000467 A1 | 1/2012 | Milne et al. |
| 2012/0000468 A1 | 1/2012 | Milne et al. |
| 2012/0000469 A1 | 1/2012 | Milne et al. |
| 2012/0000470 A1 | 1/2012 | Milne et al. |
| 2012/0029317 A1 | 2/2012 | Doyle et al. |
| 2012/0030611 A1 | 2/2012 | Skidmore |
| 2012/0060841 A1 | 3/2012 | Crawford, Jr. et al. |
| 2012/0071729 A1 | 3/2012 | Doyle et al. |
| 2012/0090611 A1 | 4/2012 | Graboi et al. |
| 2012/0096381 A1 | 4/2012 | Milne et al. |
| 2012/0133519 A1 | 5/2012 | Milne et al. |
| 2012/0136222 A1 | 5/2012 | Doyle et al. |
| 2012/0137249 A1 | 5/2012 | Milne et al. |
| 2012/0137250 A1 | 5/2012 | Milne et al. |
| 2012/0167885 A1 | 7/2012 | Masic et al. |
| 2012/0185792 A1 | 7/2012 | Kimm et al. |
| 2012/0197578 A1 | 8/2012 | Vig et al. |
| 2012/0197580 A1 | 8/2012 | Vij et al. |
| 2012/0211008 A1 | 8/2012 | Perine et al. |
| 2012/0216809 A1 | 8/2012 | Milne et al. |
| 2012/0216810 A1 | 8/2012 | Jafari et al. |
| 2012/0216811 A1 | 8/2012 | Kimm et al. |
| 2012/0226444 A1 | 9/2012 | Milne et al. |
| 2012/0247471 A1 | 10/2012 | Masic et al. |
| 2012/0272960 A1 | 11/2012 | Milne |
| 2012/0272961 A1 | 11/2012 | Masic et al. |
| 2012/0272962 A1 | 11/2012 | Doyle et al. |
| 2012/0277616 A1 | 11/2012 | Sanborn et al. |
| 2012/0279501 A1 | 11/2012 | Wallace et al. |
| 2012/0304995 A1 | 12/2012 | Kauc |
| 2012/0304997 A1 | 12/2012 | Jafari et al. |
| 2013/0000644 A1 | 1/2013 | Thiessen |
| 2013/0006133 A1 | 1/2013 | Doyle et al. |
| 2013/0006134 A1 | 1/2013 | Doyle et al. |
| 2013/0008443 A1 | 1/2013 | Thiessen |
| 2013/0025596 A1 | 1/2013 | Jafari et al. |
| 2013/0025597 A1 | 1/2013 | Doyle et al. |
| 2013/0032151 A1 | 2/2013 | Adahan |
| 2013/0042869 A1 | 2/2013 | Andrieux et al. |
| 2013/0047983 A1 | 2/2013 | Andrieux et al. |
| 2013/0047989 A1 | 2/2013 | Vandine et al. |
| 2013/0053717 A1 | 2/2013 | Vandine et al. |
| 2013/0074844 A1 | 3/2013 | Kimm et al. |
| 2013/0081536 A1 | 4/2013 | Crawford, Jr. et al. |
| 2013/0104896 A1 | 5/2013 | Kimm et al. |
| 2013/0146055 A1 | 6/2013 | Jafari et al. |
| 2013/0152923 A1 | 6/2013 | Andrieux et al. |
| 2013/0158370 A1 | 6/2013 | Doyle et al. |
| 2013/0159912 A1 | 6/2013 | Baker, Jr. |
| 2013/0167842 A1 | 7/2013 | Jafari et al. |
| 2013/0167843 A1 | 7/2013 | Kimm et al. |
| 2013/0186397 A1 | 7/2013 | Patel |
| 2013/0186400 A1 | 7/2013 | Jafari et al. |
| 2013/0186401 A1 | 7/2013 | Jafari et al. |
| 2013/0192599 A1 | 8/2013 | Nakai et al. |
| 2013/0220324 A1 | 8/2013 | Jafari et al. |
| 2013/0233319 A1 | 9/2013 | Winter et al. |
| 2013/0239967 A1 | 9/2013 | Jafari et al. |
| 2013/0255682 A1 | 10/2013 | Jafari et al. |
| 2013/0255685 A1 | 10/2013 | Jafari et al. |
| 2013/0284172 A1 | 10/2013 | Doyle et al. |
| 2013/0284177 A1 | 10/2013 | Li et al. |
| 2014/0000606 A1 | 1/2014 | Doyle et al. |
| 2014/0012150 A1 | 1/2014 | Milne et al. |
| 2014/0034054 A1 | 2/2014 | Angelico et al. |
| 2014/0123979 A1 | 5/2014 | Doyle et al. |
| 2014/0182590 A1 | 7/2014 | Platt et al. |
| 2014/0224250 A1 | 8/2014 | Sanchez et al. |
| 2014/0251328 A1 | 9/2014 | Graboi et al. |
| 2014/0261409 A1 | 9/2014 | Dong et al. |
| 2014/0261410 A1 | 9/2014 | Sanchez et al. |
| 2014/0261424 A1 | 9/2014 | Doyle et al. |

(56) References Cited

U.S. PATENT DOCUMENTS

FOREIGN PATENT DOCUMENTS

| | | |
|---|---|---|
| EP | 0850652 | 7/1998 |
| EP | 1205203 | 9/2004 |
| EP | 1205203 B1 | 9/2004 |
| EP | 1189649 | 6/2005 |
| EP | 0965357 | 3/2007 |
| EP | 2017586 | 1/2009 |
| FR | 2695320 | 3/1994 |
| JP | 2002136595 | 5/2002 |
| WO | WO 9114470 | 10/1991 |
| WO | WO 199611717 | 4/1996 |
| WO | WO 9641571 | 12/1996 |
| WO | WO 9744636 | 11/1997 |
| WO | WO 2007/102866 | 9/2007 |
| WO | WO 2007109177 | 9/2007 |

OTHER PUBLICATIONS

7200 Ventilatory System: Addendum/Errata. Nellcor Puritan Bennett, Part No. 4-023576-00, Rev. A, Apr. 1988.
800 Operator's and Technical Reference Manual. Series Ventilator System, Nellcor Puritan Bennett, Part No. 4-070088-00, Rev. L, Aug. 2010.
840 Operator's and Technical Reference Manual. Ventilator System, Nellcor Puritan Bennett, Part No. 4-075609-00, Rev. G, Oct. 2006.
Cairo et al., "Mosby's Respiratory Care Equipment, Seventh Edition", Mosby, US, XP002524651, 2004, pp. 360-361 and 775-778.
International Search Report, PCT/US2009/034363, dated Aug. 5, 2009.
International Search Report, PCT/US2009/055889, dated Nov. 26, 2009.
International Search Report, PCT/US2009/059102, dated Nov. 30, 2009.
Jaffe, Ph.D., Michael B., "Proximal Flow Measurement with the Series 3 Flow Sensors", Respironics, Inc., 2002, pp. 1-4.
PCT International Search Report dated Mar. 3, 2011, Application's File Reference H-RM-01941WO, International Application No. PCT/US2010/058265, Int'l. filing date Nov. 30, 2010, Applicant Nellcor Puritan Bennett LLC, 16 pgs.
U.S. Appl. No. 12/628,803, Office Action dated Jun. 27, 2012, 13 pgs.
U.S. Appl. No. 12/628,856, Notice of Allowance dated May 23, 2012, 8 pgs.
U.S. Appl. No. 12/628,882, Office Action dated Jul. 11, 2012, 12 pgs.
U.S. Appl. No. 12/628,905, Office Action dated Jul. 11, 2012, 13 pgs.
U.S. Appl. No. 12/628,921, Office Action dated Jun. 26, 2012, 10 pgs.
U.S. Appl. No. 29/360,553, Notice of Allowance dated Oct. 13, 2011, 8 pgs.
U.S. Appl. No. 29/360,554, Notice of Allowance dated Oct. 27, 2011, 8 pgs.
U.S. Appl. No. 29/360,554, Amendment and Response filed Jan. 6, 2012, 3 pgs.
U.S. Appl. No. 29/360,555, Notice of Allowance dated Oct. 27, 2011, 8 pgs.
U.S. Appl. No. 12/628,856, Notice of Allowance dated Sep. 4, 2012, 5 pgs.
U.S. Appl. No. 12/628,803, Office Action dated Sep. 25, 2012, 10 pgs.
U.S. Appl. No. 12/628,905, Office Action dated Nov. 8, 2012, 13 pgs.
U.S. Appl. No. 12/628,921, Office Action dated Sep. 21, 2012, 9 pgs.
U.S. Appl. No. 12/628,921, Advisory Action dated Oct. 30, 2012, 2 pgs.
U.S. Appl. No. 12/628,803, Notice of Allowance dated Nov. 19, 2012, 6 pgs.
U.S. Appl. No. 12/628,882, Office Action dated Nov. 14, 2012, 11 pgs.
U.S. Appl. No. 12/628,856, Notice of Allowance dated Dec. 10, 2012, 5 pgs.
U.S. Appl. No. 12/628,803, Notice of Allowance dated Jan. 30, 2013, 5 pgs.
U.S. Appl. No. 12/628,905, Notice of Allowance dated Feb. 5, 2013, 7 pgs.
U.S. Appl. No. 12/628,882, Notice of Allowance dated Feb. 5, 2013, 3 pgs.

* cited by examiner

MAINTAINING AN EXHALATION VALVE SENSOR ASSEMBLY

INTRODUCTION

Medical ventilators are designed to control the delivery of respiratory gas to a patient to supplement the patient's breathing efforts or to cause the inflation and deflation of a non-breathing patient's lung. Ventilators are often used in conjunction with a dual-limb patient circuit that conveys respiratory gas to a patient through a first tube referred to as the inspiratory limb and return exhaled gas from the patient through a second tube referred to as the expiratory limb.

In order to accurately control the delivery of respiratory gas, pressure in the patient circuit may be controlled so that gas is released during an exhalation phase and, typically but not always, flow is completely blocked during an inhalation phase. However, the ventilator circuit, particularly the expiratory limb that handles the patient's exhaled gas, presents a challenging environment. Challenges include controlling pressure and flow rate in the expiratory limb, monitoring the pressure and flow rate of the system, and capturing potentially contagious material that may be exhaled by the patient.

Maintaining an Exhalation Valve Sensor Assembly

The disclosure describes an exhalation valve sensor assembly. The disclosure describes a novel exhalation valve sensor assembly that is configured for refurbishing. Accordingly, the disclosure further describes systems and methods for maintaining an exhalation valve assembly, and the disclosure describes a kit for refurbishing an exhalation valve sensor assembly.

In an embodiment of an exhalation valve sensor assembly, an exhalation valve sensor assembly includes an assembly base. The assembly based includes a bottom-side of the assembly base, a top-side of the assembly base, and a passageway. The passageway extends through the bottom-side of the assembly base to the top-side of the assembly base. Additionally, a filter opening is on the top-side of the assembly base. A cylindrical well extends from the top-side of the assembly base, and the base of the cylindrical well encircles a portion of an opening of the passageway. An exhalation exhaust is attached to the cylindrical well. A is sensor coupled to at least one of the group selected from the passageway, the filter opening, and the exhalation exhaust. Additionally, the valve sensor assembly includes a recessed portion of the bottom side of the assembly base. The recessed portion includes an annular seat. A circular diaphragm is located within the cylindrical well, and an expiratory filter seal is located within the annular seat. Furthermore, a pressure sensor filter is attached to a filter grommet, and the filter grommet is operatively coupled to the filter opening.

In embodiments of a reprocessing kit, a kit includes a circular diaphragm configured for placement in a cylindrical well of an exhalation valve sensor body. The kit also includes, a seal bead extending from an outer edge of the circular diaphragm. The seal bead is configured to nest within an outer annular groove of the cylindrical well. The circular diaphragm includes an interior cylindrical nipple that extends in a same direction as the seal bead with a valve seat surface for engaging a valve seat of the exhalation valve sensor body. The kit also includes a ring-shaped filter seal with a flat surface. The ring-shaped seal is configured for placement into an annular seat of a recessed portion of the exhalation valve sensor body. The flat surface faces outward away from the annular seat of the exhalation valve sensor body. The kit includes a pressure sensor filter including a disk shaped body having an assembly base side and opposite exterior side with an assembly base nozzle extending from the assembly base side and an exterior side nozzle extending from the exterior side. The assembly base nozzle has a larger diameter than the exterior side nozzle. The assembly base nozzle is configured to attach to a filter grommet of the exhalation valve sensor body via rotation of the pressure sensor filter until the exhalation valve sensor body is flush with the disk shaped body.

Additionally, an embodiment of a method maintaining an exhalation valve sensor assembly includes. Disassembling an installed exhalation valve sensor assembly to form a disassembled exhalation valve sensor assembly. The disassembly includes removing an installed diaphragm from a well of the used exhalation valve sensor assembly. The disassembly includes removing an installed exhalation valve filter seal from an annular seat of a recessed portion of the used exhalation valve sensor assembly. The disassembly includes removing an installed pressure sensor filter from the used exhalation valve sensor assembly. The method includes disinfecting the disassembled exhalation valve sensor assembly to form a disinfected exhalation valve sensor assembly. The disinfecting includes pre-soaking the disassembled exhalation valve sensor assembly in an enzymatic solution to form a pre-soaked exhalation valve sensor assembly. The disinfecting includes rinsing the pre-soaked exhalation valve sensor assembly to form a rinsed exhalation valve sensor assembly. The disinfecting includes disinfecting the rinsed exhalation valve sensor assembly in a disinfectant solution to form a sanitized exhalation valve sensor assembly. The disinfecting includes rinsing the sanitized exhalation valve sensor assembly. The disinfecting includes immersing the sanitized exhalation valve sensor assembly in a drying agent. The method includes drying the disinfected exhalation valve sensor assembly. The method includes after the drying step, reassembling the disinfected exhalation valve sensor assembly. The reassembling includes inserting an uncontaminated pressure sensor filter into the disinfected exhalation valve sensor assembly. The reassembling includes inserting an uncontaminated exhalation valve filter seal into the annular seat of the recessed portion. The reassembling includes inserting an uncontaminated exhalation valve diaphragm into the well.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the drawings.

It is to be understood that both the foregoing general description and the following detailed description are exemplary and explanatory and are intended to provide further explanation of the claims.

DETAILED DESCRIPTION

Although the kits, apparatuses, systems, and methods discussed in detail below may be implemented for a variety of medical devices, the present disclosure will discuss these apparatuses, systems, and methods in the context of a medical ventilator for use in providing ventilation support to a human patient. The reader will understand that the technology described in the context of a medical ventilator for human patients could be adapted for use with other systems such as ventilators for non-human patients. Additionally, the technology may be used in conjunction with a general gas transport system where there is a desire to direct, monitor, and/or control the effluent flow of gas from the system.

An exhalation valve sensor assembly monitors the pressure, temperature, and/or flow of exhalation gases. However, the exhalation valve sensor assembly is directly exposed exhaled gases of a patient. The exhaled gas contains water vapor or humidity which may clog the flow paths within the exhalation valve sensor assembly. Further, the exhalation gas may contain contagious materials depending upon the patient that could contaminate the exhalation flow sensor assembly. Accordingly, there is a desire to perform maintenance on one or more elements of an exhalation valve sensor assembly.

Accordingly, this disclosure describes embodiments of exhalation valve sensor assembly that is configured to be refurbished. Additionally, the disclosure describes systems and methods for maintaining the exhalation valve sensor assembly. Further, this disclosure describes kits that include replaceable parts that aid in the maintenance of the exhalation valve sensor assembly. The refurbishable exhalation valve sensor assembly, the maintaining systems and methods, and/or the kits prevent contamination between patients. Further, the refurbishable exhalation valve sensor assembly, the maintaining systems and methods, and/or the kits may extend the life of the exhalation valve sensor assembly when compared to exhalation valve sensor assemblies that are not refurbishable.

Figure 1:
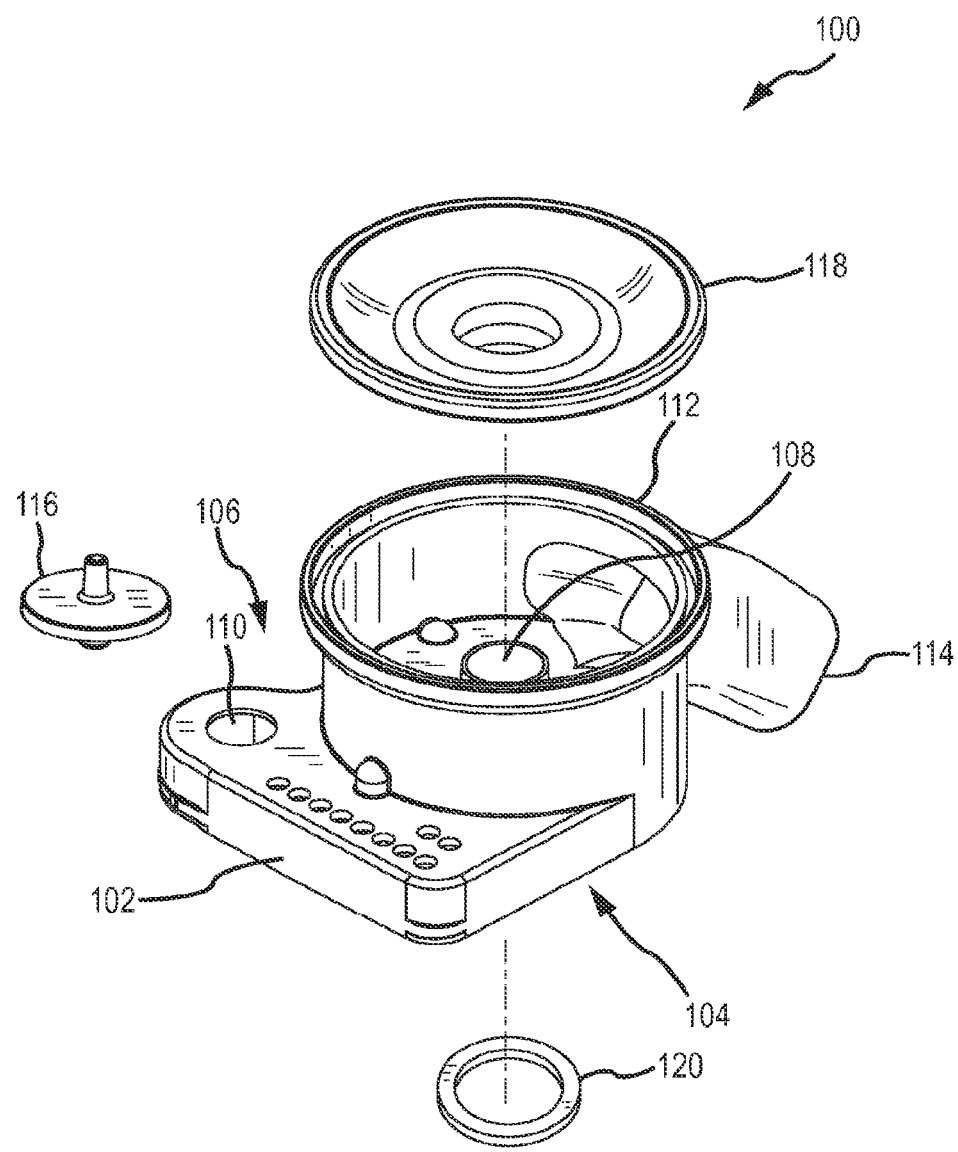
FIG. 1 illustrates an embodiment of an exploded view of an exhalation valve sensor assembly.
Figure 2:
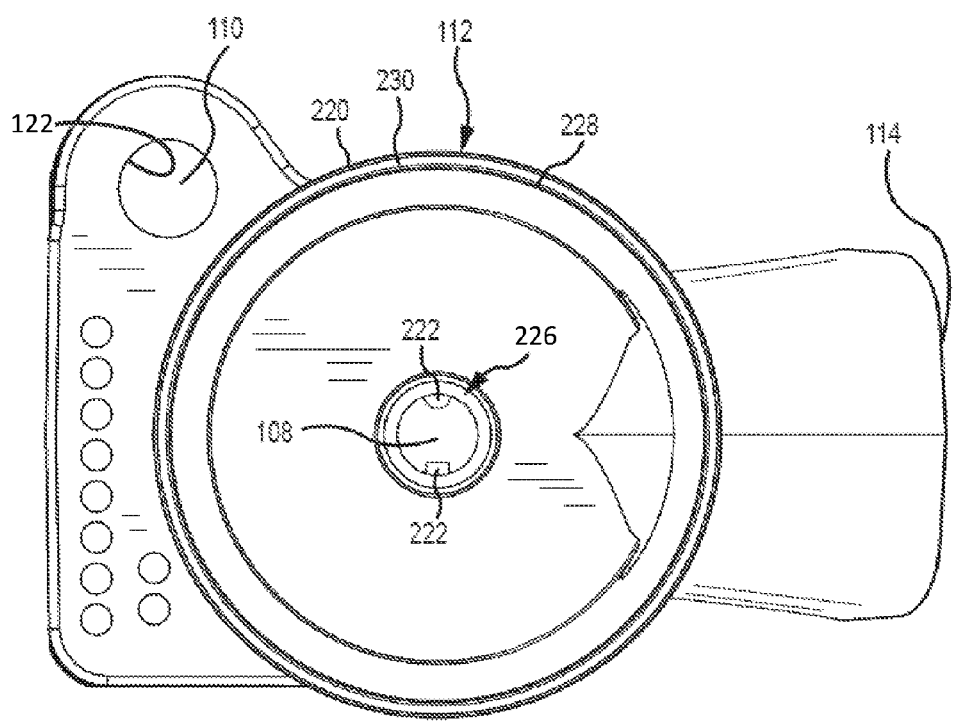
FIG. 2 illustrates an embodiment of a top view of an exhalation valve sensor body.
Figure 3:
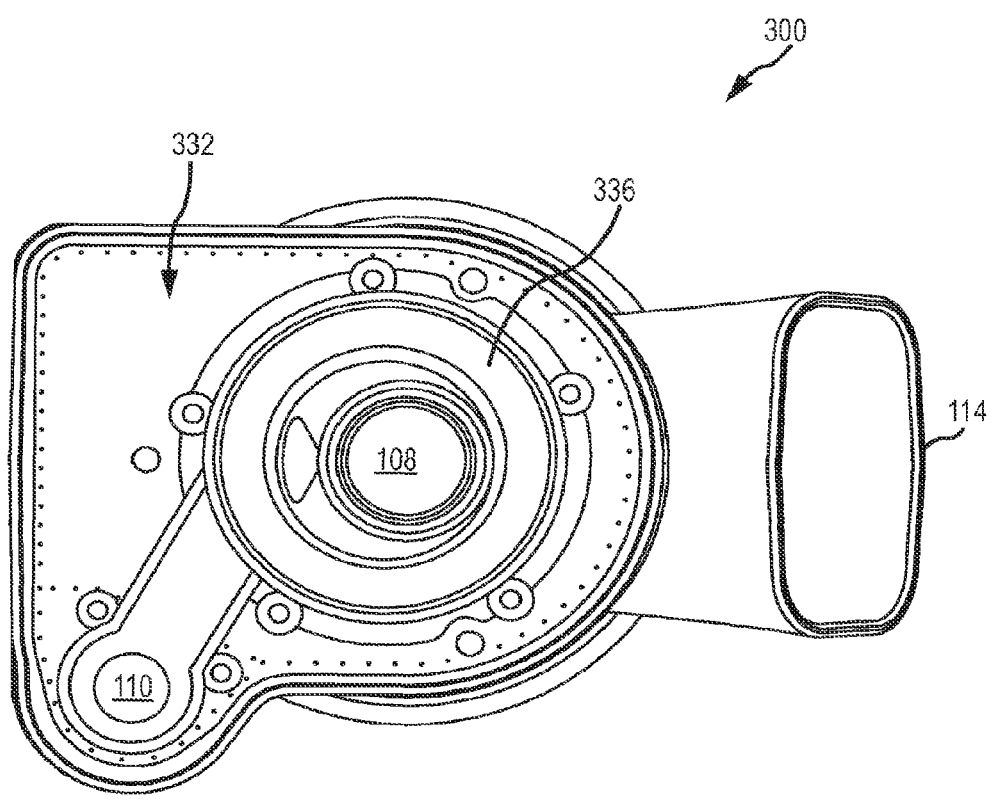
FIG. 3 illustrates an embodiment of a bottom view of an exhalation valve sensor body.

FIGS. 1-3 illustrate embodiments of an exhalation valve sensor assembly.

FIG. 1 illustrates an exhalation valve sensor assembly 100 that includes an assembly base 102. The assembly base 102 has a bottom-side 104, a top-side 106, and a passageway 108 that extends through the base and provides a flow path from the bottom-side 104 to the top-side 106. The well 112 is attached to and extends from a top-side 106 of an assembly base 102. The well 112 includes an exhalation exhaust 114. A top-side 106 also has a filter opening 110. A bottom-side 104 has a recessed portion. A device having an assembly base 102, a well 112, and an exhalation exhaust 114 may be referred to as an exhalation valve sensor body. Further, an exhalation valve sensor assembly 100 may include a pressure sensor filter 116, a diaphragm 118, and an expiratory filter seal 120.

In embodiments, both the top-side 106 and the bottom-side 104 of the assembly base 102 have substantially flat surfaces. Additionally, either or both the top-side 106 and the bottom-side 104 may have a recessed portion. A recessed portion need not contain further recesses, but the recessed portion may contain further recessed portions. Further, the top-side 106B, which is opposite the bottom-side 104, may be oriented such that the top-side and bottom-side are substantially parallel to each other.

In embodiments, a passageway 108 may allow gas to flow from a bottom-side 104 to a top-side 106. In some embodiments, the passageway 108 has a cylindrical or tubular shape. Additionally, a passageway 108 may be axially oriented perpendicular to the planes of a top-side 106 and a bottom-side 104. Such an embodiment may form a direct bore from the top-side 106 to a bottom-side 104. Additionally, a top-side opening of the passageway 108 may extend beyond a top-side 106. The extension may be substantially cylindrical or tubular in shape. The extension may extend to a height lower than that of a wall of a cylindrical well 112. Further, a passageway 108 may have a design that can engage the surface of a diaphragm. In some embodiments, the passageway 108 houses one or more temperature, pressure and/or flow sensors. In other embodiments, the passageway 108 does not include any sensors.

In embodiments, the top-side opening of the passageway 108 may be encompassed by a well 112. The well 112 may be cylindrical in shape. A cylindrical well 112 has a single wall. In embodiments where a passageway 108 has an opening that extends past a top-side 106, the height of the wall of the cylindrical well 112 may be higher than that of the height of the extended passageway 108. In embodiments, a passageway 108 allows exhaled air to flow into a well 112. Flow of exhaled air continues from well 112 out to exhalation exhaust 114. A well 112 may be attached to a base 102. Alternatively, a single piece of molded plastic may form the top-side 106 and the well 112.

A well 112 may include an exhalation exhaust 114. An exhalation exhaust 114 is any device, shape, or opening that is adapted to allow flow of gas to travel out of a well 112. For example, an exhalation exhaust 114 may extend out away from the well 112. Alternatively, the exhalation exhaust 114 may be a port. An extended exhalation exhaust 114 may have any suitable shape such as tubular, cylindrical, or parallelepiped shape. Additionally, the extended exhalation exhaust 114 may be a combination of any such shapes to form a unique 3-dimensional shape. In embodiments, an extended exhalation exhaust 114 will be adapted to allow gas to flow from the well 112 to the exhalation exhaust 114.

The exhalation exhaust 114 may direct effluent flow of gas, such as exhaled air from a user of a medical ventilator, to an open environment. This directing may be accomplished by angling an extended exhalation exhaust 114 in some direction. This direction may be a direction away from an exhalation valve sensor assembly 100. The open environment may be the environment external to a ventilator, such as the space in a room in which a person using a medical ventilator is located. Alternatively, the exhalation exhaust 114 may be coupled to another device that may further process or filter the exhaled air.

In embodiments, a filter opening 110 may be an opening to a pathway designed to allow air or another fluid to pass to a sensor device, such as flow sensor device. A pathway may be cylindrical in nature, and the filter opening 110 may be circular in shape. A filter opening 110 may be fitted with a grommet. The filter grommet may be adapted to receive a pressure sensor filter 116.

An exhalation valve sensor body including an assembly base 102, a well 112, and an exhalation exhaust 114 may be made from a rigid plastic material. For example, the rigid plastic material may be PVC. Other suitable materials may also be used to make the exhalation exhaust 114.

A pressure sensor filter 116 may filter air or other gasses for use in combination with a flow sensor. The pressure sensor filter 116 may have a disked shaped body. The disk may have two nozzles that protrude axially through the center of the disk. One nozzle may be adapted for insertion into the filter opening 110 located on the top-side 106 of the assembly base 102. In embodiments, this nozzle is known as the assembly base nozzle. The opposite side nozzle may extend outward away from the assembly base 102. In embodiments, this nozzle is known as an exterior side nozzle. Additionally, in embodiments, the side of the disk shaped body from which the assembly base nozzle extends from is known as the assembly base side. The side opposite the assembly base side from which the exterior side nozzle extends from the disk shaped body is known as the exterior base side.

The pressure sensor filter 116 may be designed to operatively couple to a filter opening 110. Operative coupling may be accomplished through the use of a filter grommet. For example, a filter grommet may contain threads that correspond to threads located on an assembly base nozzle of a pressure sensor filter 116. In embodiments, inserting and twisting a pressure sensor filter 116 into a filter opening 110 containing a threaded filter grommet may screw the pressure sensor filter 116 into the filter opening 110. Other mechanism such as a catch may also be used. Embodiments of a pressure sensor filter are described further with reference to FIG. 4.

A diaphragm 118 may be used in an exhalation valve sensor assembly 100. In embodiments, a diaphragm 118 may be circular and may have a seal bead that extends from an outer edge. A circular diaphragm 118 may additionally have a cylindrical nipple that extends outward from the center of the circular diaphragm 118. A cylindrical nipple may have a flat side that is adapted to sit on a valve seat of a passageway 108. Embodiments of a diaphragm are described further with reference to FIG. 5.

The exhalation valve sensor assembly 100 may include an expiratory filter seal 120. The expiratory filter seal 120 may be ring shaped. Additionally, a ring-shaped expiratory filter seal 120 may have a flat surface and an opposite surface. An expiratory filter seal 120 may fit in a seat of a recessed portion of a bottom side 104 of an assembly base. The flat surface of a expiratory filter seal 120 may face away from a valve sensor body. Embodiments of a filter seal are described further with reference to FIG. 6.

With reference to FIG. 2, FIG. 2 illustrates a top view of an exhalation valve sensor body 200. In embodiments, an exhalation valve sensor body 200 may include a passageway 108, a filter opening 110, a well 112, an exhalation exhaust 114, and a sensor 222.

In embodiments, devices such as a diaphragm or a one way valve may be used to intermittently block a passageway 108. The blockage may correspond to an inhalation phase of a medical ventilator. For example, during inspiration, the passageway 108 may be blocked to prevent gas from flowing from the well 112 into the passageway 108. During exhalation, the blockage created by the diaphragm may be moved to allow airflow from the passageway 108 to an exhalation exhaust 114.

In embodiments, intermittently blocking an air pathway from a passageway 108 is accomplished by use of a diaphragm. For example, the passageway 108 has a valve seat 226 that can engage a diaphragm. In an embodiment, the diaphragm is circular, and the diaphragm has an interior cylindrical nipple. The cylindrical nipple may have a flat surface. In an embodiment, the flat surface of the cylindrical nipple is such that that when the flat surface is flush with a valve seat 226, an airtight or substantially airtight seal is formed. When a diaphragm is in a resting state and inserted into a well 112, air cannot flow from the passageway 108 into the well 112. The force of air traveling from a passageway 108 may be sufficient to cause the cylindrical nipple to separate from the valve seat 226. This separation may allow air to flow from the passageway 108 to the well 112.

In embodiments a sensor 222 may be affixed to areas of an exhalation valve sensor body 200. For example, the sensor may be affixed to an inner wall of the passageway 208. A sensor 222 may be a hot wire anemometer flow meter. There may be a desire to use a hot-wire anemometers sensor 222 because of its small size. Hot wire anemometer-based sensors are known in the art, and such sensors measure flow based on the cooling of a heated wire, or based on the current required to maintain a wire at a fixed temperature when the wire is exposed to the flow of gas. Although a hot wire anemometer-based sensor is described, any suitable sensor now known or later developed may be used.

For example, a sensor 222 may be a differential pressure meter. A sensor 222 in the form of a differential pressure meter includes a pressure sensor connected to two pressure taps providing access to different points in a flow path. The flow path may be a pathway through the passageway 108, into the well 112, and out through the exhalation exhaust 114. A filter opening 110 may provide access to atmospheric pressure for a flow sensor 222. A pressure sensor filter may filter air or other gases to service a flow sensor 222. As is known in the art, flow can be determined by measuring the differential pressure across a known flow restriction under known conditions of temperature and gas characteristics. In embodiments, one or more sensors 222 may be used in combination with other sensors 222, and each sensor 222 used may be of a different type than other sensors 222. The sensor 222 may be placed in a number of locations about an exhalation valve sensor body 200. For example, sensors 222 may be placed in a filter opening, an exhalation exhaust, a passageway, and/or a well.

A well 112 includes at least one wall 220, and the well 112 may have a seal bead lip 228. In embodiments, a well 112 has a cylindrical wall 220. A cylindrical well 112 may be configured to receive a circular diaphragm. For example, an annular grove 230 may be formed by a portion of a wall 220 attached to a seal bead lip 228. The annular groove 230 may be configured to allow a seal bead from a circular diaphragm to be removable inserted into an annular grove 230.

In other embodiments, the edge of the well 112 may have one or more retainers such as lips, grooves, or ridges so that a diaphragm may be removably attached. When attached to the cylindrical well 112, a circular diaphragm may form a substantially airtight seal so gas may only flow from a passageway 108 to exhalation exhaust 114.

With respect to FIG. 3, FIG. 3 represents a bottom view of an exhalation valve sensor body 300. In embodiments, an exhalation valve sensor body 300 has a passageway 108, a filter opening 110, an exhalation exhaust 114, a recessed portion 332, and an annular seat 336.

In embodiments, an annular seat 336 may be present. The annular seat 336 may be configured to receive an expiratory filter seal. Such a seal may form a substantially airtight seal with an attached device, such as a filter trap module of a medical ventilator. This substantially airtight seal may allow air to flow from an attached device through a passageway 108 to out to an exhalation exhaust 114.

FIGS. 4, 5, 6 and 7 are illustrations of embodiments of a kit. Kits contain one or more replaceable parts of an exhalation valve sensor assembly. Kits may additionally contain instructions.

Figure 4:
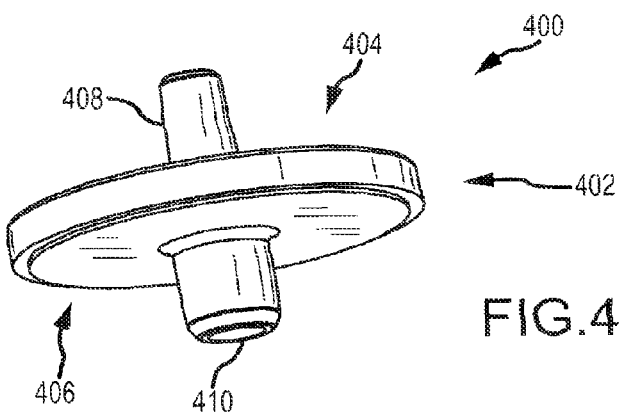
FIG. 4 illustrates an embodiment of a kit.

With reference to FIG. 4, FIG. 4 represents an embodiment of kit containing a pressure sensor filter 400. A pressure sensor filter 400 is an embodiment of a kit for replacing an installed pressure filter in an exhalation valve sensor assembly. As shown, the pressure sensor filter 400 may have a disk shaped body 402. The disk shaped body 402 has an exterior side 404 and an assembly base side 406. In embodiments, an exterior side nozzle 408 protrudes from the exterior side 404 of the disk shaped body. Additionally, an assembly base nozzle 410 protrudes from an assembly base side 406. As illustrated in FIG. 4, the assembly base nozzle 410 and the exterior side nozzle 408 have a cylindrical shape. The diameter of the opening of the assembly base nozzle 410 may be greater than that of the diameter of the opening of the exterior side nozzle 408. A passageway exists such that air can flow through an exterior side nozzle 408, into the disk shaped body 402, and through an assembly base nozzle 410. A pressure sensor filter 400 may employ a variety of filtering techniques and filter media. A pressure sensor filter 400 may be used to replace an installed pressure sensor filter during the refurbishing an exhalation valve sensor assembly.

Figure 5:
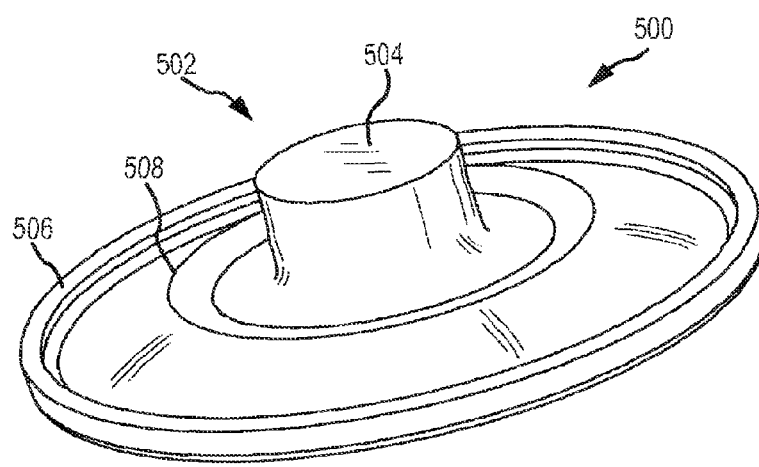
FIG. 5 illustrates an embodiment of a kit.

Turning now to FIG. 5, FIG. 5 illustrates an embodiment of a kit containing a diaphragm 500. As shown, diaphragm 500 is a circular diaphragm 500. A diaphragm 500 is an embodiment of a kit for replacing an installed diaphragm of an exhalation valve sensor assembly. The diaphragm 500 has a flexible protrusion that extends outward from the center of a circular diaphragm 500. This protrusion is known as cylindrical nipple 502. In embodiments, the cylindrical nipple 502 may have a flat surface 504 that is adapted to fit a valve seat of a passageway. Additionally, the diaphragm 500 has a seal bead 506 adapted to fit or nest within an annular grove of an exhalation valve body assembly. Further, a diaphragm may have a ring-shaped seal mounting hump 508. The diaphragm 500 is used to replace an inserted diaphragm during the refurbishing of an exhalation valve sensor assembly.

In embodiments, a kit may contain a diaphragm and an expiratory filter seal. In these embodiments, the diaphragm and the expiratory filter seal may be contained in a single package. In some embodiments, when a kit containing a diaphragm and the expiratory filter seal may utilize a ring-shaped seal mounting hump 508 to removably couple to a ring-shaped expiratory filter seal 600 to a diaphragm 500 in order to reduce packaging space. Such a coupling may be a loose coupling. For example, a ring-shaped seal 602 may be placed on a ring-shaped seal mounting hump 508. Doing so may reduce the amount of movement a ring-shaped seal 600 may experience in relationship to the diaphragm 500 when packaged during, for example, transport of a ring-shape seal 602. The ring-shaped seal may be similar or the same as the embodiment illustrated in FIG. 6.

In other embodiments, a kit may contain a diaphragm and a pressure sensor filter contained in one package. In other embodiments, the kit may contain a diaphragm, a pressure sensor filter, and an expiratory filter seal. Indeed, a kit may contain a combination of one or more types of reusable parts. Additionally, each there may be multiple reusable parts of a single type in a kit. The cylindrical nipple 502 may be configured such that one side of a pressure sensor filter nests in the cylindrical nipple 502 when packaged. The nesting may allow for a condensed packaging arrangement. For example a pressure sensor filter 400 may have an exterior side nozzle 408 that nests within the cylindrical nipple 502. Additionally, a pressure sensor filter 400 may have an assembly base nozzle 410 that nests within the cylindrical nipple 502.

In embodiments, diaphragm 500 is constructed from a unitary construction of molded, flexible material such as silicon rubber. The material may be one that resists wear and degradation. Other materials may be used such as VITON rubber, elastomers or other suitable materials.

Figure 6:
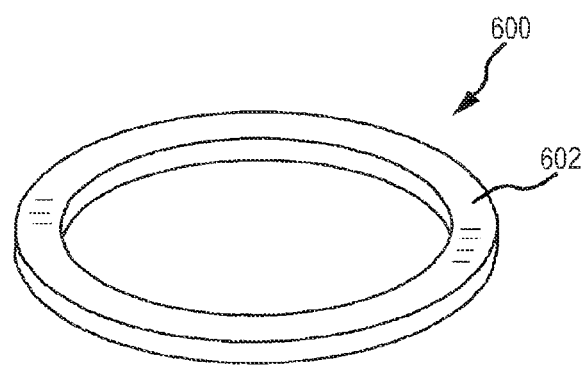
FIG. 6 illustrates an embodiment of a kit.

With respect to FIG. 6, FIG. 6 shows an embodiment of a kit containing an expiratory filter seal 600. The expiratory filter seal 600 is used to replace an installed expiratory filter seal of an exhalation valve sensor assembly. This expiratory filter seal 600 may be a ring-shaped expiratory filter seal as illustrated. A ring-shaped filter seal may have a flat-side 602 specifically adapted to interface with another device within a ventilator system. For example, the ring-shaped filter seal may form a substantially air-tight seal with another device in a ventilator system. In some embodiments, the other device is a filter-trap module. A ring-shaped expiratory filter seal 600 is placed in an annular seat of a recessed portion of a valve sensor body. This may cause a substantially air-tight seal or air-tight seal to form when an exhalation valve sensor assembly is inserted into a ventilator system. Expiratory filter seal 600 may be made of the same or similar material as those materials described above with respect to diaphragm 500.

Figure 7:
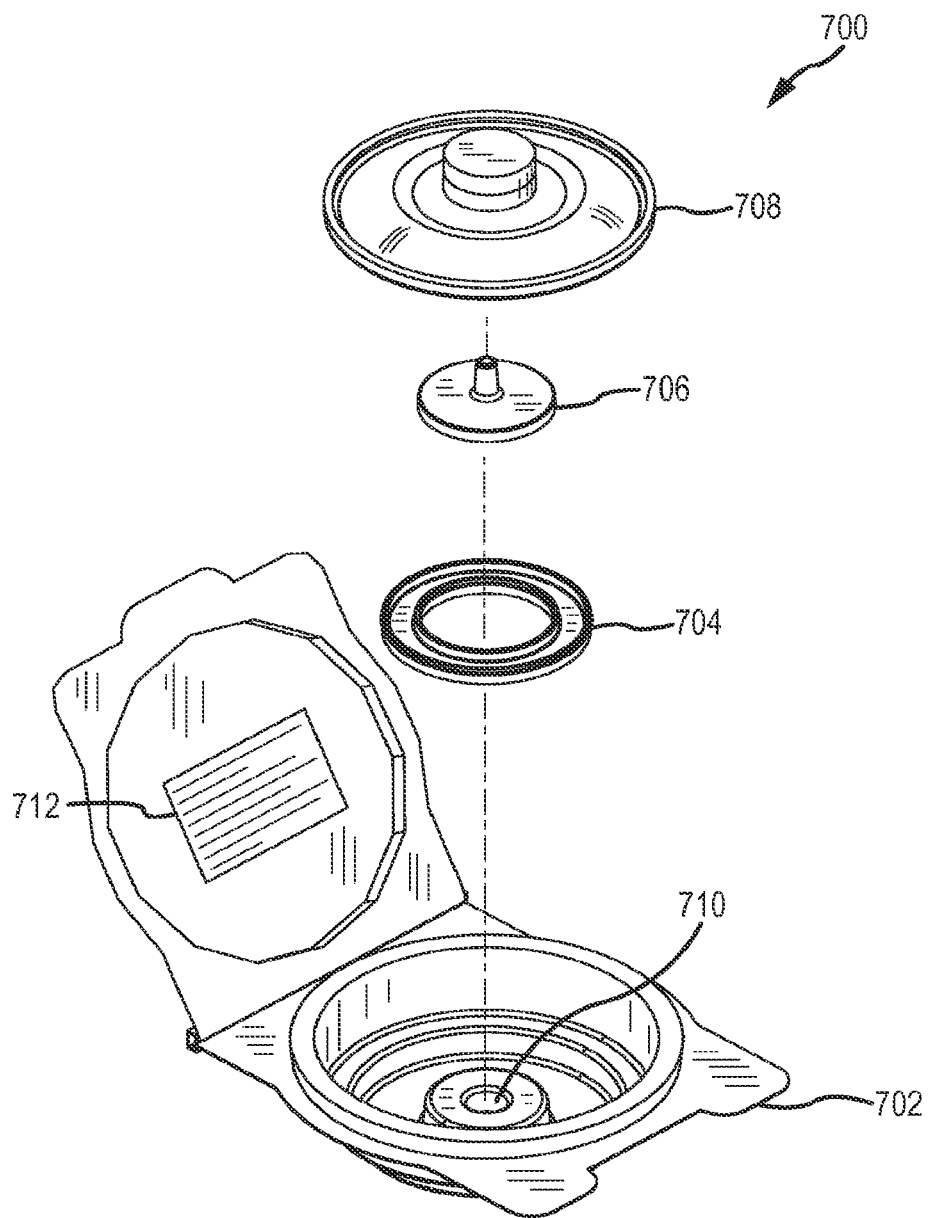
FIG. 7 illustrates an embodiment of an exploded view of a kit.

Turning now to FIG. 7, FIG. 7 illustrates an embodiment of a kit 700. A kit 700 includes a container 702, an expiratory filter seal 704, a pressure sensor filter 706, and diaphragm 708.

As illustrated, container 702 has a lid and a bottom. In some embodiments, the bottom and the lid are pivotally connected to each other. In further embodiments, container 702 is made of a rigid plastic material. For example, the container 702 may be made of PVC. Additionally other suitable materials may be used to for the container. For example, materials for preventing contamination of the kit pieces may be used, such as rubber, flexible plastics, cardboard or other materials may be used.

Other container 702 configurations may be available. For example, a container 702 may be a flexible plastic. This flexible plastic container 702 may be designed for a single use. Opening the container may involve tearing open the single use container 702 along a pre-scored edge.

The bottom portion of a container 702 may be designed to receive one or more reusable parts. For example, certain containers 702 have bottom portions, and these bottom portions have an inner well 710. An inner well 710 may be cylindrical in shape. The inner well 710 may be configured to receive an element of a reusable part. For example, a pressure sensor filter 706 may have one or more nozzles that may fit snuggly or nest into the inner well 710 of a container 702.

Inner well 710 may have an outer circular wall that is sized to receive an expiratory filter seal 704. For example, a ring-shaped expiratory filter seal 704 may have an inner-hole diameter such that the circular expiratory filter seal fits snugly around a wall of a cylindrical inner well 710. Thus the raised wall may prevent the filter seal from moving freely about the packaging shell and/or reduce packaging space and materials.

In embodiments, the raised wall of a cylindrical inner well 710 may be such that a raised wall of the cylindrical inner well 710 is configured to secure a diaphragm 708. In embodiments, a raised wall may be such that the raised wall extends into a hollow inner nipple of a diaphragm 708. This may substantially prevent the diaphragm from moving about a package. In an embodiment, the flexible nature of the diaphragm 708 may be used to provide a restraining force on the other components when installed in the container so that none of the components can move when installed in the container 702. This force may or may not require the diaphragm 708 to be stored in a deformed shape, depending on the implementation of the packaging.

It may be desirous for a container 702 to be substantially sterile. This may be achieved by manufacturing the packaging in a sterile environment. Other embodiments may cause a container 702 to become sterile, before or after installing the diaphragm 708, filter seal 704, and sensor filter 706, by any suitable means known in the art such as heat or chemical sterilization agents.

Figure 12:
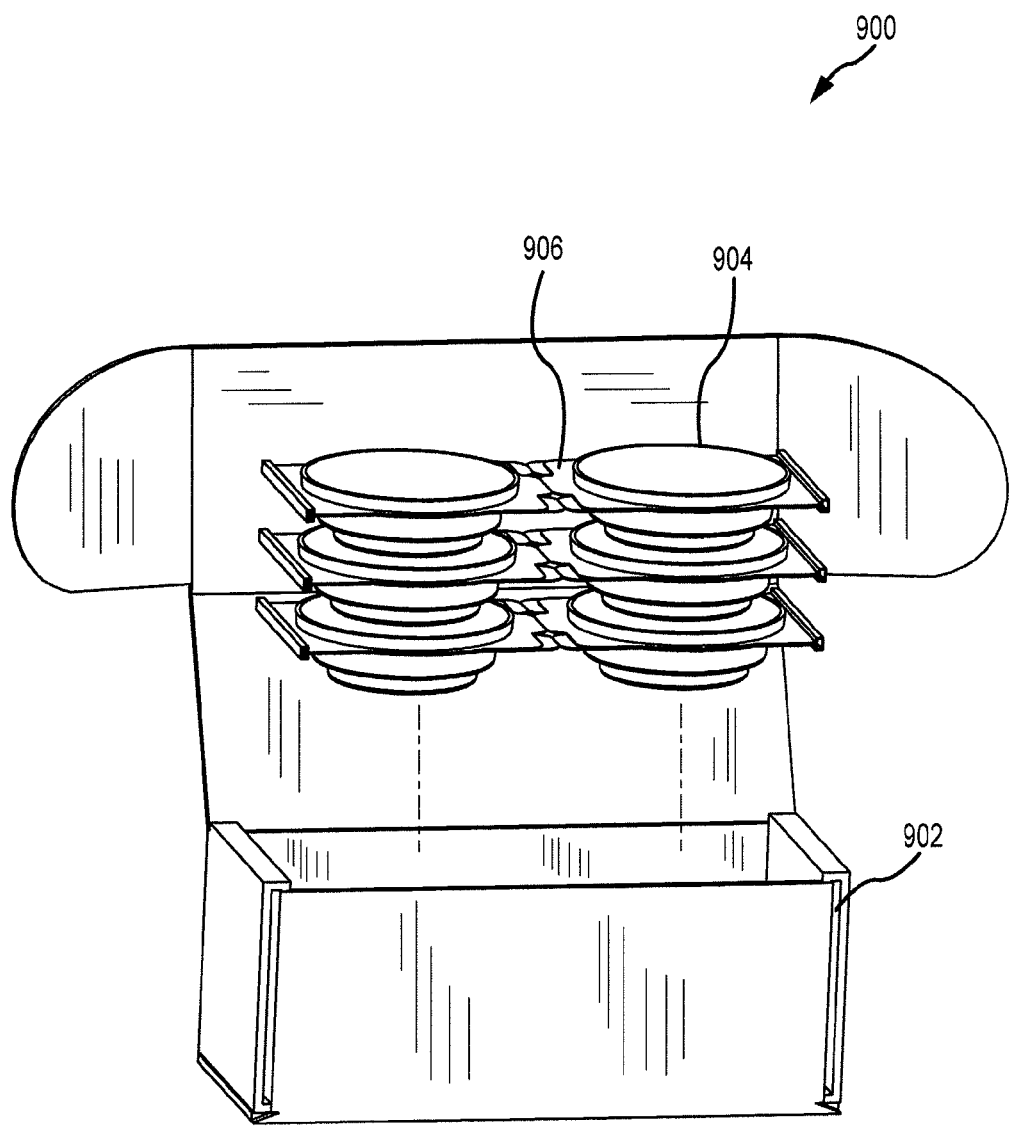
FIG. 12 illustrates an exploded view of an embodiment of a package for holding multiple kits.

Instructions may be provided with the reusable parts in a package scheme. For example, instructions 712 may be included in container 702. In an alternative embodiment, the instructions may be attached to the container 702 or provided with the container 702, such as in the packaging as shown in FIG. 12, below. These instructions may, for example, detail a method to refurbish an exhalation valve sensor assembly. This method may be similar to the method described below with reference to FIG. 8.

FIG. 12 illustrates an embodiment of a package for holding multiple kits. Kit packing scheme 900 may contain a container 902, a kit 904, and a kit connector 906.

Container 902 may be a box that can re-sealably open, such as the one illustrated in FIG. 12. A re-sealable container 902 may be a box with a lid that can reattach and/or reclose after being opened. Alternatively, the container may not be re-sealable and/or reclosable once opened. In some embodiments, a container 902 is a flexible plastic pack.

In embodiments, kit 904 may be a circular diaphragm, an expiratory filter seal, or a pressure sensor filter. In other embodiments, a kit 904 may contain one or more of the following: a circular diaphragm, an expiratory filter seal, and a pressure sensor filter. For example, the kit 904 may a kit as described with reference to FIG. 7. In a single reusable part kit packing scheme 900, a kit is made up of only one reusable part. For example, a single reusable part kit packing scheme 900 may contain one or more circular diaphragms, but may not contain a circular diaphragm and an expiratory filter seal. However, other embodiments of packing schemes include containers that contain kits, where the kits are made up of multiple reusable parts.

Figure 8:
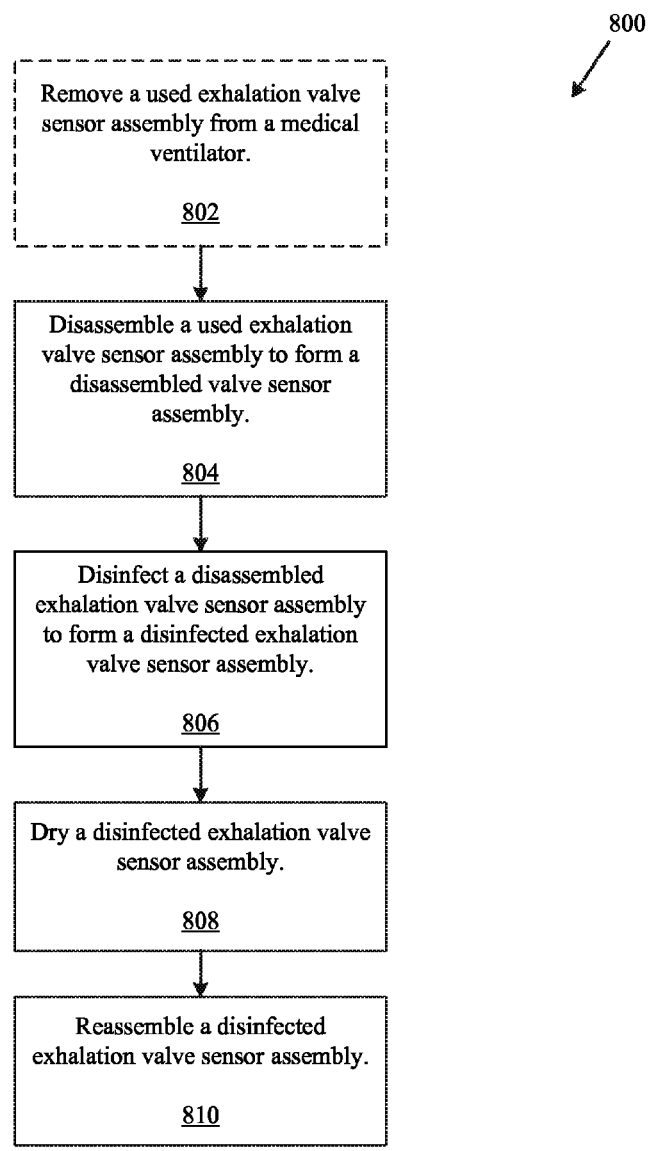
FIG. 8 illustrates a method of refurbishing an exhalation valve sensor assembly.

A kit 904 may be affixed to another kit 904 in a packing scheme 900. This may be accomplished by the use of a kit connector 906. Kit connector 906 may be a rigid plastic affixed to a kit 904. In other embodiments, multiple containers, such as multiple containers 702 are created from a single mold. These Turning now to FIG. 8, FIG. 8 provides a method 800 of refurbishing an exhalation valve sensor assembly. A patient may contaminate an exhalation valve sensor assembly. For example, expiratory gas contains humidity and biological debris. This may adhere to various parts and passageways of an exhalation valve sensor assembly. Method 800 provides a way to disinfect, clean, and/or extend the usable life of the non-disposable parts of a valve sensor assembly. Refurbishing method 800, however, need not be in response to patient use. In some embodiments method 800 is performed where the fidelity of an exhalation valve sensor assembly is questionable.

In an embodiment, refurbish method 800 begins by removing of an installed exhalation valve sensor assembly operation 802. In remove operation 802 an installed exhalation valve assembly is removed from a ventilation system. In embodiments, there may be a necessity to access an exhalation valve sensor assembly. Access may be obtained by opening a door.

Removal operation 802 may then proceed by inserting a thumb into a installed exhalation exhaust and placing four fingers into a recessed portion of the installed exhalation sensor valve assembly. Care may be taken to not place fingers into a passageway. This may ensure that any flow sensors within a passageway are not damaged.

Figure 9:
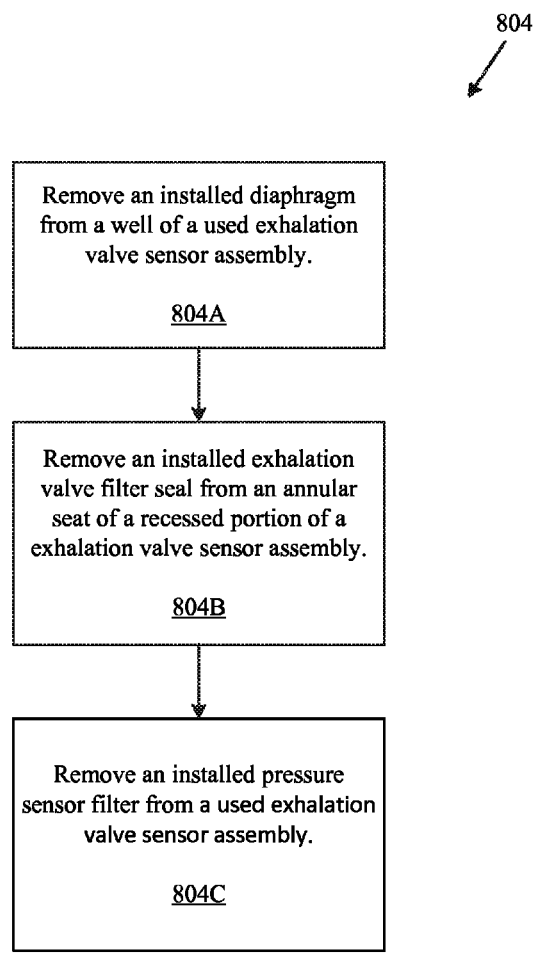
FIG. 9 illustrates a method of disassembling a used exhalation valve sensor assembly to form a disassembled valve sensor assembly.

Refurbish method 800 includes a disassemble operation 804. The disassemble operation 804 disassembles an installed exhalation valve sensor assembly to form a disassembled exhalation valve sensor assembly. As illustrated in FIG. 9, disassemble operation 804 includes a diaphragm removal operation 804A, a seal removal operation 804B, and a filter removal operation 804C. During operation 804A, an installed diaphragm is removed from a well of the used exhalation valve sensor assembly operation 804A. In some embodiments operation 804A includes lifting the installed diaphragm out of a well. Force may be needed to lift the installed diaphragm where an installed diaphragm has a seal bead inserted into an annular grove of a well of an exhalation valve sensor assembly.

During operation 804B, an installed exhalation valve filter seal is removed from an annular seat of the used exhalation valve sensor assembly. In embodiments, operation 804B includes removing an installed expiratory valve filter seal from a recessed portion of the used exhalation valve sensor assembly. This removal may be accomplished by pinching the installed expiratory filter seal between two fingers and lifting the expiratory filter seal out of an annular seat of a recessed portion of an exhalation valve sensor assembly.

During operation 804C, an installed pressure sensor filter is removed from a used exhalation valve sensor assembly. In embodiments, operation 804C includes removing the installed pressure sensor filter, which may be located in a filter grommet that is attached to a filter opening of a used exhalation valve sensor assembly. Accordingly, in this embodiment, the installed pressure sensor is removed by using a twisting motion during operation 804C. In other embodiments, the installed pressure sensor filter is removed by lifting the pressure sensor filter out of a filter opening during operation 804C.

Removal of the disposable parts including an installed diaphragm, an installed valve filter seal, and an installed pressure filter need not occur in any particular order during disassemble operation 804. The term "installed" refers to a disposable part (such as a diaphragm, a pressure sensor filter, and an exhalation valve filter seal) that was installed in an exhalation valve sensor assembly. The exhalation valve sensor assembly containing the installed disposable part may or may not have been used in a medical ventilation device. The medical ventilator containing the installed disposable part may or may not have been used in the treatment of a patient. In some embodiments, the installed disposable part may be contaminated. The removal of the disposable parts creates a disassembled exhalation valve sensor assembly.

The disposable parts may contain bio-contaminated waste. When bio-contamination is present, it is important to dispose of the disposable parts according to local governing ordinances regarding the disposal of potentially bio-contaminated waste.

Figure 10:
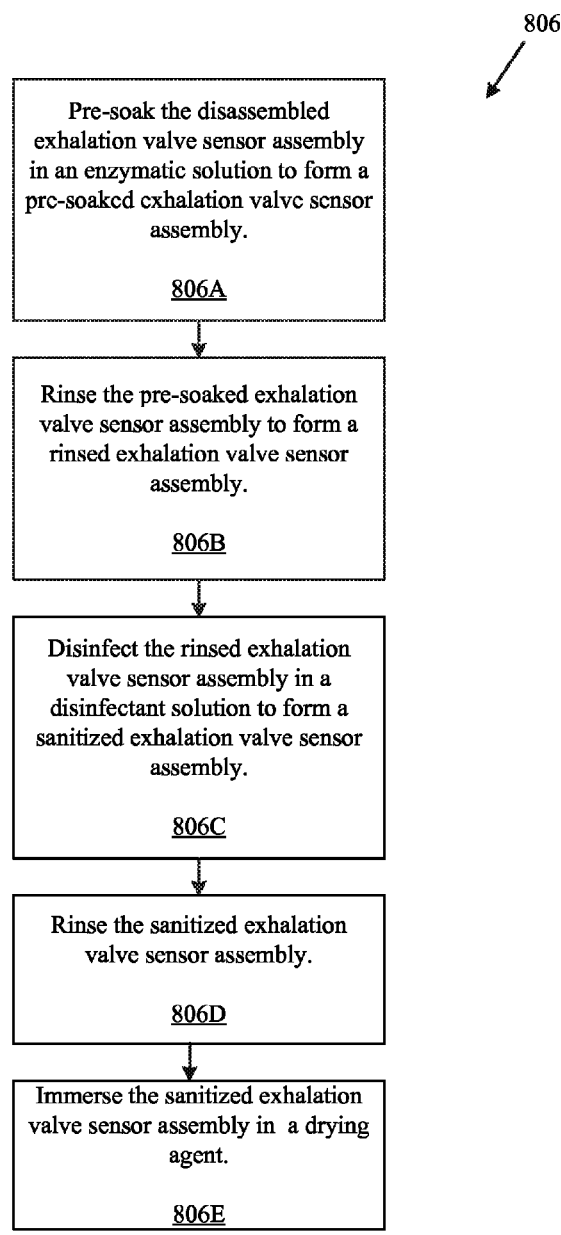
FIG. 10 illustrates a method of disinfecting a disassembled exhalation valve sensor assembly to form a disinfected exhalation valve sensor assembly.

Refurbish method 800 then proceeds to disinfect operation 806. Disinfect operation 806 includes pre-soaking the disassembled exhalation valve sensor assembly in an enzymatic solution to form a pre-soaked exhalation valve sensor assembly operation 806A, rinsing the pre-soaked exhalation valve sensor assembly to form a rinsed exhalation valve sensor assembly operation 806B, disinfecting the rinsed exhalation valve sensor assembly in a disinfectant solution to form a sanitized exhalation valve sensor assembly operation 806C, rinsing the sanitized exhalation valve sensor assembly operation 806D, and immersing the sanitized exhalation valve sensor assembly in a drying agent operation 806E. Completion of these steps forms a disinfected exhalation valve sensor assembly. Disinfect valve sensor operation is illustrated in FIG. 10.

In embodiments, disinfect operation 806 includes pre-soaking a disassembled exhalation valve sensor assembly in an enzymatic solution operation 806A. Pre-soaking the disassembled exhalation valve sensor assembly may break down any bio-film that may be present. Presoaking a disassembled exhalation valve sensor assembly operation 806A creates a pre-soaked exhalation sensor valve assembly.

In embodiments, disinfect operation 806 includes rinsing a disassembled exhalation valve sensor assembly operation 806B. The rinsing agent may be deionized water or other suitable rinsing agent. Rinsing operation 806B forms a rinsed exhalation valve sensor assembly.

In embodiments, disinfect operation 806 includes disinfecting a disassembled exhalation valve sensor assembly by immersion in a disinfectant solution operation 806C. Disinfecting operation 806C may include preparing a suitable disinfectant.

In embodiments, disinfecting by immersion operation 806C of a rinsed exhalation valve sensor assembly may include orienting the rinsed exhalation valve sensor assembly such that the exhalation exhaust is pointed toward the surface of the disinfectant. Next, one then immerses the disassembled exhalation valve sensor in the disinfectant. While immersed, one then rotates the rinsed exhalation valve sensor until all trapped air contained within the rinsed exhalation valve is removed. The immersion operation 806C forms a sanitized exhalation valve sensor assembly.

The next step in disinfect operation 806 is rinsing a sanitized exhalation valve sensor assembly 806D. This may help to remove any excess disinfectant. The rinsing agent may be deionized water or other suitable rinsing agent. In some embodiments of the method 800, there is a necessity to perform this rinsing several times, including three times.

The next step in disinfect operation 806 is immersing the sanitized exhalation valve sensor assembly in a drying agent operation 806E. Operation 806E the drying agent may be isopropyl alcohol or other suitable agent. One may immerse the sanitized exhalation valve sensor for approximately 15 seconds. Slowly swishing and rotating the sanitized exhalation valve sensor assembly may remove air from air pockets. After this step, the sanitized exhalation valve sensor assembly may be referred to as a disinfected valve sensor assembly. After a disinfect operation 806 various parts of the disinfected valve sensor assembly may be described as disinfected. For example, after a disinfect operation 806, the disinfected valve sensor assembly includes a disinfected well, a disinfected filter opening, and a disinfected annular seat.

Refurbish method 800 then proceeds to a drying operation 808. Operation 808 includes drying a disinfected valve sensor assembly. Drying the disinfected valve sensor assembly may proceed in a low temperature warm air cabinet designed for such purposes. It may be desirable to ensure the temperature does not exceed 140 df.

Figure 11:
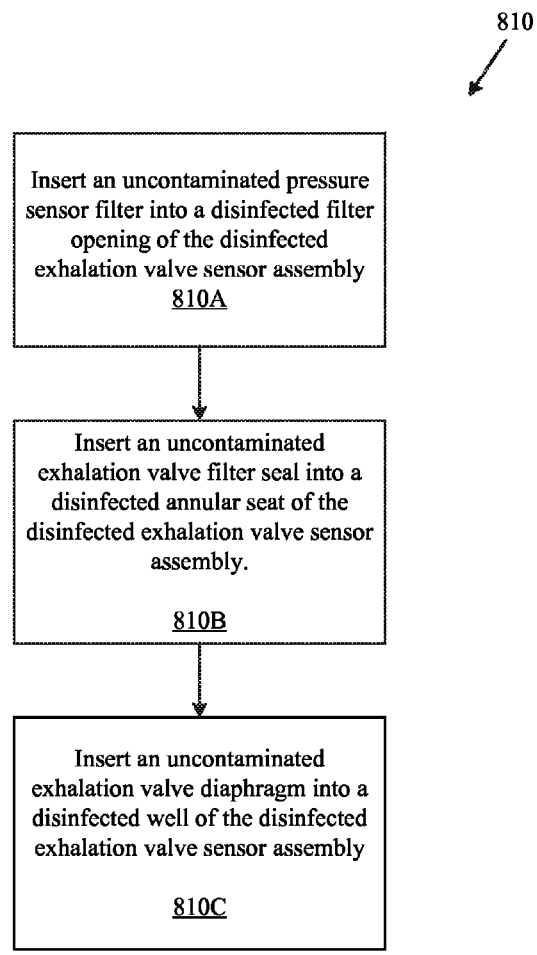
FIG. 11 illustrates a method of reassembling a disinfected exhalation valve sensor assembly.

After the drying step, refurbish method 800 may proceed to a reassemble operation 810. Operation 810 includes reassembling a disinfected exhalation valve sensor assembly, which is illustrated in FIG. 11. This includes inserting an uncontaminated pressure sensor filter into a disinfected filter opening of the disinfected exhalation valve sensor assembly 810A, inserting an uncontaminated exhalation valve filter seal into a disinfected annular seat of the disinfected exhalation valve sensor assembly 810B, and inserting an uncontaminated exhalation valve diaphragm into a disinfected well of the disinfected exhalation valve sensor assembly 810C.

It will be clear that the systems and methods described herein are well adapted to attain the ends and advantages mentioned as well as those inherent therein. Those skilled in the art will recognize that the methods and systems within this specification may be implemented in many manners and as such is not to be limited by the foregoing exemplified embodiments and examples. In other words, functional elements being performed by a single or multiple components and individual functions can be distributed among different components. In this regard, any number of the features of the different embodiments described herein may be combined into one single embodiment and alternate embodiments having fewer than or more than all of the features herein described as possible.

While various embodiments have been described for purposes of this disclosure, various changes and modifications may be made which are well within the scope of the disclosed methods. Numerous other changes may be made which will readily suggest themselves to those skilled in the art and which are encompassed in the spirit of the disclosure.

What is claimed:

1. A reprocessing kit for reprocessing an exhalation valve sensor assembly, the kit comprising:
    a circular diaphragm configured for placement in a cylindrical well that extends from a top side of a base of the exhalation valve sensor assembly, wherein a seal bead extends from an outer edge of the circular diaphragm and is configured to nest within an outer annular groove of the cylindrical well, and wherein the circular diaphragm includes an interior cylindrical nipple that extends in a same direction as the seal bead with a valve seat surface for engaging a valve seat of the exhalation valve sensor assembly;
    a ring-shaped filter seal with a flat surface configured for placement into an annular seat of a recessed portion of the exhalation valve sensor assembly, wherein the flat surface faces outward away from the annular seat of the exhalation valve sensor assembly; and
    a pressure sensor filter including a disk shaped body having an assembly base side and opposite exterior side with an assembly base nozzle extending from the assembly base side and an exterior side nozzle extending from the exterior side, wherein the assembly base nozzle has a larger diameter than the exterior side nozzle, and further wherein the assembly base nozzle is configured to be received by a filter opening on the top side of the base exterior to the cylindrical well and configured to attach to a filter grommet within the exhalation valve sensor assembly via rotation of the pressure sensor filter until the top side of the base exterior to the cylindrical well of the exhalation valve sensor assembly is flush with the disk shaped body;

a container holding the circular diaphragm, the ring-shaped filter seal, and the pressure sensor filter, wherein a bottom of the container includes a cylindrical inner well with an outer circular wall, wherein the ring-shaped filter seal fits around the outer circular wall, and wherein the assembly base nozzle fits within the cylindrical inner well.

2. The reprocessing kit of claim 1, wherein the circular diaphragm, the ring-shaped filter seal, and the pressure sensor filter are configured to replace an installed circular diaphragm, an installed ring-shaped filter seal, and an installed pressure sensor filter.

3. The reprocessing kit of claim 1, wherein the container prevents contamination of the circular diaphragm, the ring-shaped filter seal, and the pressure sensor filter.

4. The reprocessing kit of claim 3, wherein the container is a sterile container.

5. The reprocessing kit of claim 4, wherein the container is a rigid container, and further wherein the rigid container includes a lid.

6. The reprocessing kit of claim 1, wherein the interior cylindrical nipple, when the pressure sensor filter is installed in the container with the circular diaphragm and the ring-shaped filter seal, extends from a center of the circular diaphragm, and wherein the exterior side nozzle of the pressure sensor filter nests within the interior cylindrical nipple of the circular diaphragm.

7. The reprocessing kit of claim 1, further comprising instructions on how to perform a method of refurbishing the exhalation valve sensor assembly.

8. The reprocessing kit of claim 7, wherein the instructions detail how to insert the circular diaphragm, the pressure sensor filter, and the ring-shaped filter seal in the exhalation valve sensor assembly.

9. The reprocessing kit of claim 1, wherein the circular diaphragm includes a seal mounting hump.

10. The reprocessing kit of claim 9, wherein the ring-shaped filter seal, when installed in the container with the circular diaphragm and the pressure sensor filter, fits loosely on the seal mounting hump.

11. The reprocessing kit of claim 10, wherein the assembly base nozzle of the pressure sensor filter, when the pressure sensor filter is installed in the container with the circular diaphragm and the ring-shaped filter seal, nests within the interior cylindrical nipple.

12. A reprocessing kit for reprocessing an exhalation valve sensor assembly, the kit comprising:

a circular diaphragm configured for placement in a cylindrical well of an exhalation valve sensor assembly, wherein a seal bead extends from an outer edge of the circular diaphragm and is configured to nest within an outer annular groove of the cylindrical well, and wherein the circular diaphragm includes an interior cylindrical nipple that extends in a same direction as the seal bead with a valve seat surface for engaging a valve seat of the exhalation valve sensor assembly;

a ring-shaped filter seal with a flat surface configured for placement into an annular seat of a recessed portion of the exhalation valve sensor assembly, wherein the flat surface faces outward away from the annular seat of the exhalation valve sensor assembly;

a pressure sensor filter including a disk shaped body having an assembly base side and opposite exterior side with an assembly base nozzle extending from the assembly base side and an exterior side nozzle extending from the exterior side, wherein the assembly base nozzle has a larger diameter than the exterior side nozzle, and further wherein the assembly base nozzle is configured to attach to a filter grommet of the exhalation valve sensor assembly via rotation of the pressure sensor filter until the exhalation valve sensor assembly is flush with the disk shaped body;

a container for holding the circular diaphragm, the ring-shaped filter seal, and the pressure sensor filter, wherein the container includes a lid and a bottom, wherein the bottom includes a cylindrical inner well with an outer circular wall, wherein the outer circular wall is configured to allow the ring-shaped filter seal to fit around the outer circular wall, and wherein the cylindrical inner well is configured to allow the assembly base nozzle to fit within the cylindrical inner well.

13. A reprocessing kit for reprocessing an exhalation valve sensor assembly, the kit comprising:

a circular diaphragm configured for placement in a cylindrical well of an exhalation valve sensor assembly, wherein a seal bead extends from an outer edge of the circular diaphragm and is configured to nest within an outer annular groove of the cylindrical well, and wherein the circular diaphragm includes an interior cylindrical nipple that extends in a same direction as the seal bead with a valve seat surface for engaging a valve seat of the exhalation valve sensor assembly;

a ring-shaped filter seal with a flat surface configured for placement into an annular seat of a recessed portion of the exhalation valve sensor assembly, wherein the flat surface faces outward away from the annular seat of the exhalation valve sensor assembly;

a pressure sensor filter including a disk shaped body having an assembly base side and opposite exterior side with an assembly base nozzle extending from the assembly base side and an exterior side nozzle extending from the exterior side, wherein the assembly base nozzle has a larger diameter than the exterior side nozzle, and further wherein the assembly base nozzle is configured to attach to a filter grommet of the exhalation valve sensor assembly via rotation of the pressure sensor filter until the exhalation valve sensor assembly is flush with the disk shaped body;

a container for holding the circular diaphragm, the ring-shaped filter seal, and the pressure sensor filter, wherein the interior cylindrical nipple, when the pressure sensor filter is installed in the container with the circular diaphragm and the ring-shaped filter seal, extends from a center of the circular diaphragm, and wherein the exterior side nozzle of the pressure sensor filter nests within the interior cylindrical nipple of the circular diaphragm.

* * * * *